United States Patent
Mayo

(10) Patent No.: US 9,200,333 B2
(45) Date of Patent: Dec. 1, 2015

(54) METHODS FOR IDENTIFYING MODULATORS OF MURINE DOUBLE MINUTE 2

(71) Applicant: Indiana University Research and Technology Corporation, Indianapolis, IN (US)

(72) Inventor: Lindsey Mayo, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 7 days.

(21) Appl. No.: 13/950,825

(22) Filed: Jul. 25, 2013

(65) Prior Publication Data
US 2014/0030726 A1    Jan. 30, 2014

Related U.S. Application Data

(60) Provisional application No. 61/675,631, filed on Jul. 25, 2012.

(51) Int. Cl.
| | | |
|---|---|---|
| *G01N 1/00* | (2006.01) | |
| *C12Q 1/68* | (2006.01) | |
| *G01N 33/68* | (2006.01) | |
| *C12Q 1/25* | (2006.01) | |

(52) U.S. Cl.
CPC .............. *C12Q 1/6897* (2013.01); *C12Q 1/25* (2013.01); *G01N 33/6875* (2013.01); *G01N 2333/9015* (2013.01); *G01N 2440/00* (2013.01); *G01N 2440/14* (2013.01); *G01N 2500/10* (2013.01)

(58) Field of Classification Search
None
See application file for complete search history.

(56) References Cited

U.S. PATENT DOCUMENTS

2012/0115892 A1    5/2012 Dezube et al.

OTHER PUBLICATIONS

Khosravi et al., PNAS, 1999, vol. 96, pp. 14973-14977.*
Maya et al., Genes & Development, 2001, vol. 15, pp. 1067-1077.*
Zhou et al., Nature Cell Biology, 2001, vol. 3, pp. 973-982.*
Xiridomas et al., Cell, 2004, vol. 118, pp. 83-97.*
Waning et al., Pharmaceuticals, 2010, vol. 3, pp. 1576-1593.*
Arasada, R.R., et al., (2005). Secretase-dependent tyrosine phosphorylation of Mdm2 by the ErbB-4 intracellular domain fragment. J Biol Chem 280, 30783-30787.
Biscardi, J.S., et al., (2000). Tyrosine kinase signalling in breast cancer: epidermal growth factor receptor and c-Src interactions in breast cancer. Breast Cancer Res 2, 203-210.
Blattner, C., et al., (2002). Hypophosphorylation of Mdm2 augments p53 stability. Mol Cell Biol 22, 6170-6182.
Boerner, J.L., et al., (2004). Phosphorylation of Y845 on the epidermal growth factor receptor mediates binding to the mitochondrial protein cytochrome c oxidase subunit II. Mol Cell Biol 24, 7059-7071.
Chairatvit, K., et al., (2007). Control of cell proliferation via elevated NEDD8 conjugation in oral squamous cell carcinoma. Mol Cell Biochem 306, 163-169.
Cher, M.L., et al., (2003). Maspin expression inhibits osteolysis, tumor growth, and angiogenesis in a model of prostate cancer bone metastasis. Proc Natl Acad Sci U S A 100, 7847-7852.
Cooper, J.A., et al., (1986). Tyr527 is phosphorylated in pp60c-src: implications for regulation. Science 231, 1431-1434.
Dias, S.S., et al., (2006). c-Abl phosphorylates Hdm2 at tyrosine 276 in response to DNA damage and regulates interaction with ARF. Oncogene 25, 6666-6671.
Dohmesen, et al., (2008). Specific inhibition of Mdm2- mediated neddylation byTip60. Cell Cycle 7,222-231.
Eitel, J.A., et al., (2009). PTEN and p53 are required for hypoxia induced expression of maspin in glioblastoma cells. Cell Cycle 8, 896-901.
Goldberg, Z., et al., (2002). Tyrosine phosphorylation of Mdm2 by c-Abl: implications for p53 regulation. EMBO J 21, 3715-3727.
Handeli, S., et al., (1992). The ts41 mutation in Chinese hamster cells leads to successive S phases in the absence of intervening G2, M, and G1. Cell 71, 599-611.
Hojo, T., et al., (2001). Association of maspin expression with the malignancy grade and tumor vascularization in breast cancer tissues. Cancer Lett 171, 103-110.
Kloth, M.T., et al., (2003). STAT5b, a Mediator of Synergism between c-Src and the Epidermal Growth Factor Receptor. J Biol Chem 278, 1671-1679.
Korkolopoulou, P., et al., (1997). MDM2 and p53 expression in gliomas: a multivariate survival analysis including proliferation markers and epidermal growth factor receptor. Br J Cancer 75, 1269-1278.
LaRusch, G.A., et al., (2007). Nutlin3 blocks vascular endothelial growth factor induction by preventing the interaction between hypoxia inducible factor 1alpha and Hdm2. Cancer Res 67, 450-454.
Liakopoulos, D., et al., (1998). A novel protein modification pathway related to the ubiquitin system. EMBO J 17, 2208-2214.
Lindstrom, M.S., et al., (2007). Cancer-associated mutations in the MDM2 zinc finger domain disrupt ribosomal protein interaction and attenuate MDM2-induced p53 degradation. Mol Cell Biol 27, 1056-1068.
Lyapina, S., et al., (2001). Promotion of NEDD-CUL1 conjugate cleavage by COP9 signalosome. Science 292, 1382-1385.
Manning, et al., (2007). AKT/PKB signaling: navigating downstream. Cell 129, 1261-1274.

(Continued)

*Primary Examiner* — Michele K Joike
*Assistant Examiner* — Mindy G Brown
(74) *Attorney, Agent, or Firm* — Stinson Leonard Street LLP

(57) ABSTRACT

The disclosure is directed to methods of identifying compounds that modulate murine double-minute 2. More particularly, the disclosure is directed to methods of identifying compounds that modulate murine double-minute 2 neddylation activity.

20 Claims, 26 Drawing Sheets

(56) References Cited

OTHER PUBLICATIONS

Mayo, L.D., et al., (2001). A phosphatidylinositol 3-kinase/Akt pathway promotes translocation of Mdm2 from the cytoplasm to the nucleus. Proc Natl Acad Sci USA 98, 11598-11603.

Momand, J., et al., (1992). The mdm-2 oncogene product forms a complex with the p53 protein and inhibits p53-mediated transactivation. Cell 69, 1237-1245.

Mukhopadhyay, D., et al., (1995). Hypoxic induction of human vascular endothelial growth factor expression through c-Src activation. Nature 375, 577-581.

Okamoto, K., Let al., (2002), Cyclin G recruits PP2A to dephosphorylate Mdm2. Mol Cell 9, 761-771.

Paliwal, P., et al., (2007). Regulation of p73 by Hck through kinase-dependent and independent mechanisms. BMC Mol Biol 8, 45.

Pan, Z.Q., et al., (2004). Nedd8 on cullin: building an expressway to protein destruction. Oncogene 23, 1985-1997.

Ralhan, R., et al., (2000). Induction of MDM2-P2 transcripts correlates with stabilized wild-type p53 in betel- and tobacco-related human oral cancer. Am J Pathol 157, 587-596.

Rayburn, E. et al., (2005). MDM2 and human malignancies: expression, clinical pathology, prognostic markers, and implications mplications for chemotherapy. Curr Cancer Drug Targets 5, 27-41.

Rodriguez, M.S., et al., (1999). SUMO-1 modification activates the transcriptional response of p53. EMBO J 18, 6455-6461.

Schlaepfer, D.D., et al., (2004). Multiple connections link FAK to cell motility and invasion. Curr Opin Genet Dev 14, 92-101.

Schwartz, D., et al., (2005). An iterative statistical approach to the identification of protein phosphorylation motifs from large-scale data sets. Nat Biotechnol 23, 1391-1398.

Shalloway, D., et al., (1984). Overexpression of the c-src protein does not induce transformation of NIH 3T3 cells. Proc Natl Acad Sci U S A 81, 7071-7075.

Shi, H.Y., et al., (2001). Blocking tumor growth, invasion, and metastasis by maspin in a syngeneic breast cancer model. Cancer Res 61, 6945-6951.

Skomedal, H., et al., (1999). Aberrant expression of the cell cycle associated proteins TP53, MDM2, p21, p27, cdk4, cyclin D1, RB, and EGFR in cervical carcinomas. Gynecol Oncol 73, 223-228.

Soucy, T.A., et al. (2009). An inhibitor of NEDD8-activating enzyme as a new approach to treat cancer. Nature 458, 732-736.

Takami, K., et al., (1994). Low Grade Amplification of MDM2 Gene in a Subset of Human Breast Cancers without p53 Alterations. Breast Cancer 1, 95-102.

Xirodimas, D.P. (2008). Novel substrates and functions for the uhiquitin-like molecule NEDD8. Biochem Soc Trans 36, 802-806.

Xirodimas, D.P., et al., (2004). Mdm2-mediated NEDD8 conjugation of p53 inhibits its transcriptional activity. Cell 118, 83-97.

Yeatman, T.J. (2004). A renaissance for SRC. Nat Rev Cancer 4, 470-480.

Zeng, X., et al., (1999). MDM2 suppresses p73 function without promoting p73 degradation. Mol Cell Biol 19, 3257-3266.

Zhang, M., et al., (2000). Maspin is an angiogenesis inhibitor. Nat Med 6, 196-199.

Zou, Z., et al., (1994). Maspin, a serpin with tumor-suppressing activity in human mammary epithelial cells. Science 263, 526-529.

Zou, Z., et al., (2000). p53 regulates the expression of the tumor suppressor gene maspin. J Biol Chem 275, 6051-6054.

Lehman, JA et al., (2011), Induction of Apoptotic Genes by a p73-Phosphatase and Tensin Homolog (p73-PTEN) Protein Complex in Response to Genotoxic Stress. J. Biol. Chem. 286, 36631-36640.

Noon, AP et al., (2011), Combined p53 and MDM2 biomarker analysis shows a unique pattern of expression associated with poor prognosis in patients with renal cell carcinoma undergoing radical nephrectomy. BJU Int. 109, 1250-1257.

Waning DL, et al., (2011), c-Abl Phosphorylation of Mdm2 Facilitates Mdm2-Mdmx Complex Formation. J. Biol. Chem. 286, 216-222.

Waning, DL et al., (2010), Controlling the Mdm2-Mdmx-p53 Circuit. Pharmaceuticals (Basel) 3(5), 1576-1593.

\* cited by examiner

METHODS FOR IDENTIFYING MODULATORS OF MURINE DOUBLE MINUTE 2

CROSS-REFERENCE TO RELATED APPLICATIONS

This application claims priority from U.S. Provisional Patent Application Ser. No. 61/675,631, filed on Jul. 25, 2012, which is herein incorporated by reference in its entirety.

BACKGROUND OF THE DISCLOSURE

The present disclosure relates generally to assays and methods for identifying inhibitors for the treatment of cancers. More particularly, the present disclosure relates to screening assays and methods for identifying neddylation inhibitors for treating cancers, tumor suppressor activators in a cancer, and identifying inhibitors of tumor-induced angiogenesis.

c-Src is one of the nine members of the Src-family kinases. c-Src is a cytoplasmic non-receptor tyrosine kinase that is a critical initiation site for multiple signal transduction pathways and interactions. c-Src activation has been implicated in a multitude of tumor progression properties including survival, apoptosis, angiogenesis, migration, and adhesion. While c-Src is rarely mutated in human cancers, aberrant activation is correlated with a clinical progression of cancer and high levels are seen in a number of human tumors. However, tumorigenesis is usually in coordination with another oncogene, such as Her2 in breast cancer, since c-Src alone is not a strong transforming agent.

One of the downstream effectors of c-Src is the survival factor Akt. Akt has been shown to phosphorylate many substrates to promote cell survival including the murine double minute-2 protein (Mdm2) Mdm2 undergoes nuclear translocation in response to Akt phosphorylation at serines 166 and 186. Once in the nucleus, Mdm2 binds to the tumor suppressor p53 and inhibits its transcriptional activity along with functioning as an E3 ubiquitin ligase to signal nuclear export and proteasomal degradation. While normally kept at low levels, p53 is stabilized through post-translational modifications to both itself and Mdm2 in response to genotoxic stress. Mdm2 can also regulate p53 function by conjugation of Nedd8. This modification results in a stable, but a transcriptionally inactive p53.

Nedd8 is a part of the ubiquitin-like protein family. In a similar fashion to the ubiquitin system, neddylation involves the activation and transfer of Nedd8 from E1 (APP-BP1 in human), E2 (Ubc12), and multiple E3 RING ligases and can be removed by de-neddylating enzymes, such as COPS, CSN, NEDP1. The Nedd8 pathway has been demonstrated to be important for viability in mice, *C. elegans*, and *S. pombe*. In addition, the mammalian cell line TS-41, which has a temperature sensitive mutation in the SMC gene (APP-BP1 in human), participates in multiple rounds of DNA replication without entering a mitotic cycle. Nedd8 conjugation has been shown to be upregulated in certain types of cancer and recently a general inhibitor of the Nedd8 pathway, MLN4924, has been developed. Inhibition of global neddylation leads to apoptotic death in human cancer cells and suppresses the growth of human tumors in mouse xenografts.

In the tumor microenvironment, there are numerous growth factors and cytokines secreted from various invading cells and the stroma. This signaling leads to p53 levels that are generally not lower, but elevated. This suggests that the Mdm2-mediated destabilization of p53 was not functional. The present disclosure is directed to a Mdm2/c-Src pathway leading to activation of Mdm2 neddylation. Accordingly, Mdm2 activity presents an alternative mechanism for identifying targeted cancer therapies.

SUMMARY OF THE DISCLOSURE

The present disclosure relates generally to methods for identifying modulators of Murine double minute 2. Murine double-minute 2 (Mdm2) phosphorylation by c-Src results in increased neddylation of tumor suppressors such as, for example, p53, and decreases the expression of its downstream target, Maspin. Increased neddylation through Mdm2 results in the inhibition of tumor suppressor activity, which may lead to tumor growth, invasion, metastasis, and tumor-induced angiogenesis. It has now been discovered that Mdm2 neddylation activity can be used in screening assays to identify modulators of Mdm2 It has also been discovered that Mdm2 phosphorylation can be used in screening assays to identify compounds that modulate Mdm2 activity.

In one aspect, the present disclosure is directed to a method of identifying a compound that modulates murine double-minute neddylation. The method includes providing a cell transfected with a nucleic acid encoding murine double-minute; contacting the cell with a test compound; and determining murine double-minute phosphorylation.

In another aspect, the present disclosure is directed to a method of identifying a compound that modulates murine double-minute activity. The method includes contacting murine double-minute with a protein kinase and a test compound; and determining murine double-minute phosphorylation.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1A:
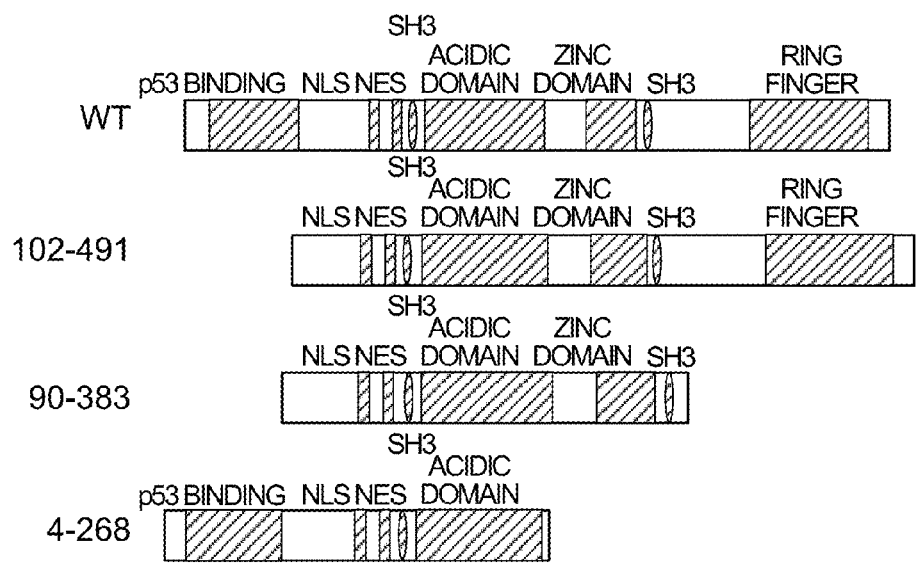
FIG. 1A is a schematic depicting truncation mutants of Mdm2 as described in Example 2.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, a novel Mdm2/c-Src pathway leading to activation of Mdm2 neddylation has been identified. Accordingly, Mdm2 activity presents alternative mechanisms for targeted cancer therapies. More particularly, methods have been discovered that allow for the treatment of cancer by inhibiting Mdm2 neddylation activity. In many embodiments, the methods may be used to treat cancers such as, for example, prostate cancer, breast cancer, gliomas, neuroblastomas, osteosarcomas, leukemias, lymphomas, pancreatic cancer, oral cancer, renal cancer, and cervical cancer. Thus, the methods may be used to halt, slow and/or reverse the onset or progression of one or more of these cancers in individuals. The methods include administration of neddylation inhibitors to an individual in need thereof specifically afflicted with these cancers or at risk of developing these cancers due to heredity or other factors (e.g., experimental induction). As such, in some embodiments, the methods disclosed herein are directed to a subset of the general population, including experimental animals, such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases or conditions.

In one aspect, the present disclosure is directed to a method of treating cancer in an individual in need thereof. The method includes administering a therapeutically effective amount of a neddylation inhibitor. Suitable therapeutically effective amounts for animals may be about 30 mg/kg to about 60 mg/kg. A particularly suitable therapeutically effective amount for a human may be about 50 mg/m$^2$.

As used herein, the terms "therapeutically effective amount", "effective amount", and "effective" are used interchangeably and are intended to designate a dose that causes a relief of symptoms of a disease or condition as noted through clinical testing and evaluation, patient observation, and/or the like, and/or a dose that causes a detectable change in biological or chemical activity. The detectable changes may be detected and/or further quantified by those skilled in the art for the relevant mechanism or process. As is generally understood in the art, the dosage will vary depending on the administration routes, symptoms and body weight of the patient and may also depend upon the compound being administered.

Administration of a therapeutically effective amount may be by a single dose, multiple doses, as part of a dosage regimen, and combinations thereof as determined by those skilled in the art for the relevant mechanism or process. The dosage may vary depending on the symptoms, age and body weight of the patient, the nature and severity of the disorder to be treated or prevented, the route of administration and the form of the drug.

Neddylation inhibitors may be administered by any method known to those skilled in the art. Suitable methods for administering the neddylation inhibitor may be, for example, orally, injected (e.g., intravenously, intraperitoneally, intramuscularly, and subcutaneously), drop infusion preparations, ointments, drops, and the like Inhibitors prepared as described herein may be administered in various forms, depending on the disorder to be treated and the age, condition, and body weight of the patient, as is well known in the art.

Neddylation inhibitors may be administered as pharmaceutical compositions and pharmaceutically acceptable formulations that include pharmaceutically acceptable carriers. As used herein, the phrase "pharmaceutically acceptable" refers to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient.

Pharmaceutically acceptable carriers may be, for example, excipients, vehicles, diluents, and combinations thereof. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent.

Suitable neddylation inhibitors selectively inhibit Mdm2 neddylation activity. Particularly suitable neddylation inhibitors may be, for example, MLN4924.

Mdm2 protein functions to conjugate a Nedd8 molecule to a tumor suppressor to inactivate its transcriptional activity without affecting its protein stability. Thus, in one particular embodiment the neddylation inhibitor selectively inhibits neddylation of a tumor suppressor. In another embodiment, the neddylation inhibitor selectively activates a tumor suppressor. The tumor suppressor may be, for example, p53, maspin, p73, pVHL (Von Hippel-Lindau protein) and combinations thereof.

The cancer may be characterized by detection of Mdm2 Mdm2 is typically not detected in normal tissue, and thus, detection of Mdm2 in tumors is of concern. Mdm2 may be detected by methods known by those skilled in the art. Immunohistochemistry is particularly suitable for detecting Mdm2. Other methods for detecting Mdm2 may be, for example, BCA (bicinchoninic acid) assay, Lowry protein assay, ultraviolet absorbance, Bradford dye assay, densitometry of SDS-polyacrylamide gels, and other methods.

The cancer to be treated by administering the neddylation inhibitor may be, for example, prostate cancer, breast cancer, gliomas, neuroblastomas, osteosarcomas, leukemias, lymphomas, pancreatic cancer, oral cancer, renal cancer, and cervical cancer.

In another aspect, the present disclosure is directed to a method of activating a tumor suppressor in a cancer. The method includes administering an effective amount of a neddylation inhibitor.

Particularly suitable cancers may be, for example, prostate cancer, breast cancer, gliomas, neuroblastomas, osteosarcomas, leukemias, lymphomas, pancreatic cancer, oral cancer, renal cancer, and cervical cancer.

Particularly suitable tumor suppressors that may be selectively activated by administering a neddylation inhibitor may be, for example, p53, maspin, p73, pVHL and combinations thereof. The neddylation inhibitor selectively inhibits Mdm2, which leads to inhibition of neddylation of the tumor suppressor (see FIG. 37).

In another aspect, the present disclosure is directed to a method of inhibiting tumor-induced angiogenesis in an individual in need thereof. The method includes administering an effective amount of a neddylation inhibitor.

In one embodiment, the neddylation inhibitor selectively inhibits Mdm2.

In another embodiment, the neddylation inhibitor selectively activates a tumor suppressor. Particularly suitable tumor suppressors may be, for example, p53, maspin, p73, pVHL and combinations thereof.

In another embodiment, administering an effective amount of a neddylation inhibitor decreases tumor angiogenesis. Decreased tumor angiogenesis may be determined, for example, by a decrease in vascular staining, a decrease in vascular endothelial growth factor (VEGF), and combinations thereof. The transcription factor hypoxia inducible factor (HIF) is a major inducer of angiogenesis and the loss of HIF results in decreased angiogenesis. Vascular staining may be determined, for example, by methods known to those skilled in the art such as, for example, immunostaining for vascular-associated cells, proteins, and combinations thereof, histological staining, for example using hematoxylin and eosin, and other tissue and cell staining methods. A decrease in VEGF may be determined by methods known to those skilled in the art such as, for example, polymerase chain reaction, Northern blotting, Southern blotting, Western blotting, and combinations thereof.

In another aspect, the present disclosure is directed to a method of identifying a compound that modulates murine double-minute 2 neddylation. The method includes providing a cell transfected with a nucleic acid (e.g., a cDNA) encoding murine double-minute 2; contacting the cell with a test compound; and determining murine double-minute 2 phosphorylation.

Phosphorylation can be determined using methods known by those skilled in the art. Suitable methods can be, for example, Western blot (immunoblot) analysis, mass spectrometry, immunoprecipitation and combinations thereof.

In one particular embodiment, murine double-minute 2 phosphorylation is increased. Murine double-minute 2 phosphorylation can be increased at one or more of Y281 and Y302.

In one particular embodiment, murine double-minute 2 phosphorylation is decreased. Murine double-minute phosphorylation can be decreased at one or more of Y281 and Y302.

The method can further include determining murine double-minute 2 neddylation activity. Murine double-minute 2 protein functions to conjugate a Nedd8 molecule to a tumor suppressor to inactivate its transcriptional activity without affecting its protein stability. Thus, in one particular embodiment, the test compound selectively inhibits neddylation of a tumor suppressor. In another particular embodiment, the test compound selectively increases neddylation of a tumor suppressor. The tumor suppressor can be, for example, p53, maspin, p73, Von Hippel-Lindau and combinations thereof.

In another particular embodiment, murine double-minute 2 neddylation activity selectively decreases neddylation of a tumor suppressor. The tumor suppressor can be, for example, p53, maspin, p73, Von Hippel-Lindau and combinations thereof.

Neddylation can be determined by methods known by those skilled in the art. Suitable methods can be, for example, pulldown assays.

In one particular embodiment, the cell is an MCF7 (or MCF-7) cell, which is a commercially available human breast cancer cell line. In another embodiment, the cell is a H1299 (or NCI-H1299 or CRL-5803 cell) cell, which is a commercially available human non-small cell lung carcinoma cell line.

In one embodiment, the cell can be transfected with a nucleic acid encoding, for example, Cellular Rouse sarcoma viral oncogene homolog (c-Src), p53, Ableson tyrosine kinase, Ableson-related protein and Hematopoietic cell kinase. In one particular embodiment, the c-Src is a constitutively active c-Src.

In another aspect, the present disclosure is directed to a method of identifying a compound that modulates murine double-minute 2 activity. The method includes contacting murine double-minute 2 with a protein kinase and a test compound; and determining murine double-minute 2 phosphorylation.

Phosphorylation can be determined using methods known by those skilled in the art. Suitable methods can be, for example, Western blot (immunoblot) analysis, mass spectrometry, immunoprecipitation and combinations thereof.

In one embodiment, murine double-minute 2 phosphorylation is increased. Murine double-minute 2 phosphorylation can be increased at one or more of Y281 and Y302.

In another embodiment, murine double-minute 2 phosphorylation is decreased. Murine double-minute phosphorylation can be decreased at one or more of Y281 and Y302.

The protein kinase can be, for example, Cellular Rouse sarcoma viral oncogene homolog (c-Src), p53, Ableson tyrosine kinase, Ableson-related protein and Hematopoietic cell kinase.

In another embodiment, the method further includes determining murine double-minute 2 ubiquitination of a tumor suppressor.

In one embodiment, murine double-minute 2 ubiquitination of the tumor suppressor is increased in the presence of the test compound. The tumor suppressor can be, for example, p53, maspin, p73, Von Hippel-Lindau and combinations thereof.

In another embodiment, murine double-minute 2 ubiquitination of the tumor suppressor is decreased in the presence of the test compound. The tumor suppressor can be, for example, p53, maspin, p73, Von Hippel-Lindau and combinations thereof.

In another embodiment, murine double-minute 2 neddylation of hypoxia inducible factor (HIF) such as, HIF1α, can be decreased in the presence of the test compound.

Ubiquitination can be determined by methods known by those skilled in the art. Suitable methods can be, for example, pulldown assays, Western blot (immunoblot) analysis, mass spectrometry, immunoprecipitation and combinations thereof.

In another embodiment, the method further includes determining murine double-minute 2 neddylation of a tumor suppressor. The tumor suppressor can be, for example, p53, maspin, p73, Von Hippel-Lindau and combinations thereof. In one embodiment, murine double-minute 2 neddylation of the tumor suppressor is increased in the presence of the test compound. In another embodiment, murine double-minute 2 neddylation of the tumor suppressor is decreased in the presence of the test compound.

Neddylation can be determined by methods known by those skilled in the art. Suitable methods can be, for example, pulldown assays, Western blot (immunoblot) analysis, mass spectrometry, immunoprecipitation and combinations thereof.

The disclosure will be more fully understood upon consideration of the following non-limiting Examples.

EXAMPLES

Experimental Procedures

Cell Culture and Treatments

Mammalian cells (H1299 and MCF7) were cultured at 37° C. in a humidified incubator with 5% $CO_2$ in DMEM high glucose plus 10% FBS. Transfection in H1299 was performed using a calcium phosphate method and in MCF7 using Lipofectamine Plus reagent (Invitrogen). Equal amounts of DNA were transfected into cells and incubated for the indicated times prior to analysis. PPI (Calbiochem) and MLN4924 (LifeSensors) were used at concentrations provided. Site-directed mutagenesis was performed by PCR, and constructs were sequenced in their entirety.

Luciferase Assays

For the luciferase assays, H1299 and MCF7 cells were transfected with PG13-Luc, Mdm2-P2-Luc, Maspin-Luc or Mutant Maspin-Luc (MT1) along with Myc-LacZ for determination of β-galactosidase activity, using the calcium phosphate method. Reporter activity was normalized to β-galactosidase activity. Data generated were done in triplicate and standard deviation was calculated from the mean.

Protein Analysis and Immunoprecipitation

Whole cell lysates (Lysates) were prepared in Nonidet P-40 lysis buffer (25 mM Tris, pH 8.0, 150 mM NaCl, 0.5 mM EDTA, 0.5 mM EGTA, 1% Nonidet P-40, 1 mM sodium orthovanadate, 1 mM DTT) and supplemented with protease inhibitor mixture set III (Calbiochem) at 1:100 and incubated on ice for 30 min. Debris was collected by centrifugation, and equal amounts of supernatant protein were determined by BioRad assay. Protein was fractionated by SDS-PAGE and transferred to PVDF membrane (Amersham Biosciences). Antibodies used for Western blotting were: Mdm2 (SMP14, 2Al0, and 4Bl1), c-Src (B-12; Santa Cruz), p53 (DO-1), tubulin (TU-02), GAPDH (8C2), and β-actin (C4; Santa Cruz Biotechnology); phosphotyrosine (4010; Upstate); phospho-c-Src Tyr$^{416}$ (Cell Signaling); Myc (9E10) and HA (12CA5) Immunoprecipitation from lysates was performed using 500 ng of either SMP14 for Mdm2, HA (12CA5), p53 (D01) or c-Src (B-12) antibody overnight at 4° C. in 700 μl of PBS. Protein A/G Plus Agarose (Santa Cruz Biotechnology) was added to the mixture and incubated an additional 2 hrs at 4° C., precipitates were washed three times in PBS, and samples were resuspended in SDS loading buffer and boiled for 5 min.

In Vitro Reactions

All recombinant proteins were produced and purified from BL-21DE3 cells. Proteins were bound to nickel beads in Buffer A (25 mM Hepes, 0.2% Triton X-100, 5 mM DTT, 1M KCl) and then washed extensively in Buffer B (Buffer A+10 mM Imidazole). Proteins were eluted in Buffer C (Buffer A+300 mM Imidazole) and dialyzed into Buffer D (50 mM HEPES pH 7.5, 100 mM NaCl, 10% glycerol, 1 mM DTT). Recombinant GST-tagged proteins were purified over a 2 ml glutathione column. In vitro Src and Abl kinase reactions were performed at 37° C. for 30 min in kinase buffer (25 mM Tris, pH 7.4, 10 mM $MgCl_2$, 1 mM $MnCl_2$, 0.5 mM DTT, 10 μM ATP) using 0.5 mg of Src (Calbiochem) or Abl (Invitrogen). For in vitro ubiquitination assay; 500 ng of p53 was incubated with 50 ng E1 (Boston Biochem), 200 ng Ubch5a (Boston Biochem), and 1 mg ubiquitin (Boston Biochem) in the presence of 500 ng phosphorylated or unphosphorylated Mdm2 Reactions were performed for 2 hours at 37° C.

His-Ubiquitin and His-Nedd8 Pulldown Assays

H1299 cells were transfected with His-Ubiquitin or His-Nedd8 and other plasmids as indicated using calcium phosphate method. 48 hours after transfection, cells were lysed in 1 ml of 6M guanidinium-HCl, 0.1M $Na_2HPO_4/NaH_2PO_4$, 0.01M Tris-HCl pH 8.0 plus 5 mM Imidazole and 10 mM β-mercaptoethanol. After sonication, the lysates were mixed with 30 μl of $Ni^{2+}$-NTA-agarose beads (Qiagen) prewashed with lysis buffer and incubated for 2 hours at room temperature. The beads were successively washed and eluted.

Statistical Analysis

All statistical analysis was done using a two-tailed t-test with unequal variance.

Example 1

In this Example, Mdm2 binding to SH3 domains of tyrosine kinases was determined.

Recombinant Mdm2 was incubated on a SH3 domain array (Panomics, Inc., Fremont, Calif.). As shown in Table 1, Mdm2 bound to c-Abl, Abl2, c-Src and Hck-specific SH3 domains.

TABLE 1

| Mdm2 binding to SH3 Domain Array. | | |
|---|---|---|
| Symbol | Name | Mdm2 Bound |
| c-Abl | Ableson tyrosine kinase | + |
| Abl2 | Ableson-related protein (ARG) | + |
| BLK | B lymphocyte specific protein tyrosine kinase | |
| BTK | Burton's tyrosine kinase | |
| Hck | Hematopoietic cell kinase | + |

TABLE 1-continued

Mdm2 binding to SH3 Domain Array.

| Symbol | Name | Mdm2 Bound |
|---|---|---|
| IIK | Interleukin 2 inducible T-cell kinase | |
| LCK | Human T-lymphocyte specific tyrosine kinase | |
| c-Src | Cellular Rouse sarcoma viral oncogene homolog | + |
| SLK | Proto-oncogene tyrosine protein kinase FYN | |
| TXK | Tyrosine-protein kinase | |

+ indicates a positive interaction with Mdm2.

Example 2

In this Example, recombinant Mdm2 truncation mutants were made to determine the specific Mdm2 domains required for SH3-Src binding.

Figure 1B:
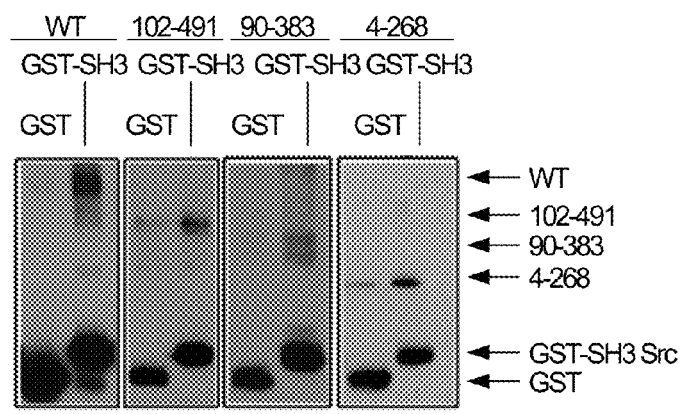
FIG. 1B is a Western blot of a GST-pulldown assay using recombinant GST or GST-SH3-Src and recombinant truncated Mdm2 proteins as described in Example 2.
Figure 2:
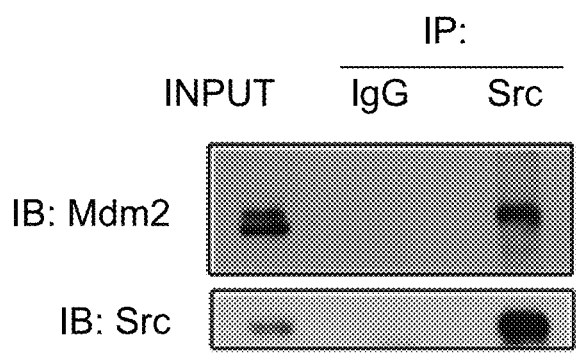
FIG. 2 is a Western blot of Src and Mdm2 from immunoprecipitation of endogenous c-Src from MCF7 cell extracts as described in Example 2.

Specifically, a series of His-tagged recombinant Mdm2 truncation mutants were made (FIG. 1A). These Mdm2 mutants were incubated in a GST-pulldown assay with either GST or the GST-SH3 domain of Src (SH3-Src). As depicted in FIG. 1B, all Mdm2 mutants were effectively pulled down with the SH3-Src domain, but not by GST alone. These results indicated that the portion of Mdm2 that interacts with Src is between residues 102-268. To further validate this interaction and determine if the interaction occurs in vivo, an immunoprecipitation of endogenous Src from MCF7 cells was performed. Western blot analysis for Mdm2 and c-Src of the immunoprecipitation reaction demonstrated that Mdm2 and c-Src were immunoprecipitated in a complex (FIG. 2).

Example 3

In this Example, an in vitro kinase reaction was performed using $^{32}$P γ-labeled ATP to determine if c-Src could phosphorylate Mdm2.

Figure 3:
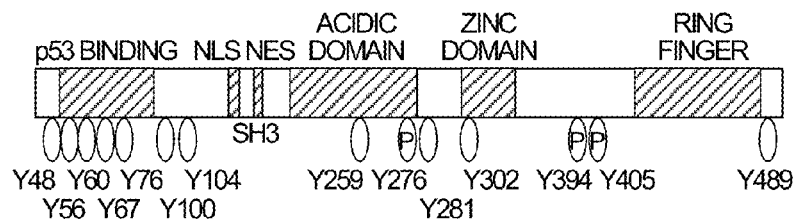
FIG. 3 is a schematic depicting tyrosines and the known tryosine phosphorylation sites (P) in Mdm2 as described in Example 3.
Figure 4:
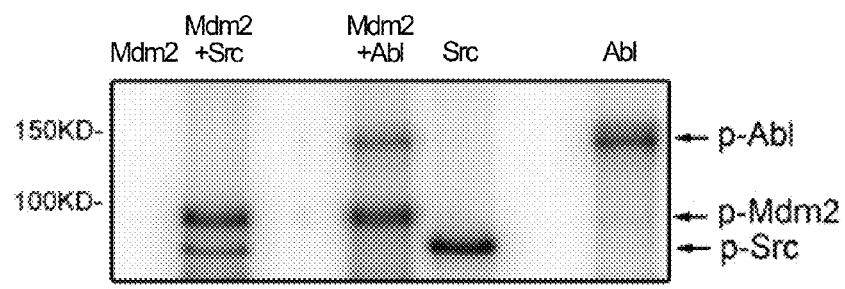
FIG. 4 is an autoradiograph of $^{32}P$ incorporation in an in vitro kinase reaction of Mdm2 (p-Mdm2) by c-Src or c-Abl as described in Example 3.

The Mdm2 protein has 14 tyrosine residues, 3 of which are identified as sites for phosphorylation by c-Abl (see, FIG. 3). Mdm2 was incubated alone, with c-Src or with c-Abl as a positive control. Mdm2 was phosphorylated by c-Abl. Mdm2 was also phosphorylated by c-Src, providing evidence that Mdm2 is a substrate for Src. (FIG. 4).

Example 4

In this Example, an in vitro kinase reaction was performed using $^{32}$P γ-labeled ATP and the Mdm2 truncation mutants (FIG. 1A) of Example 2 to determine which tyrosine residue (s) are phosphorylated by c-Src.

Figure 5:
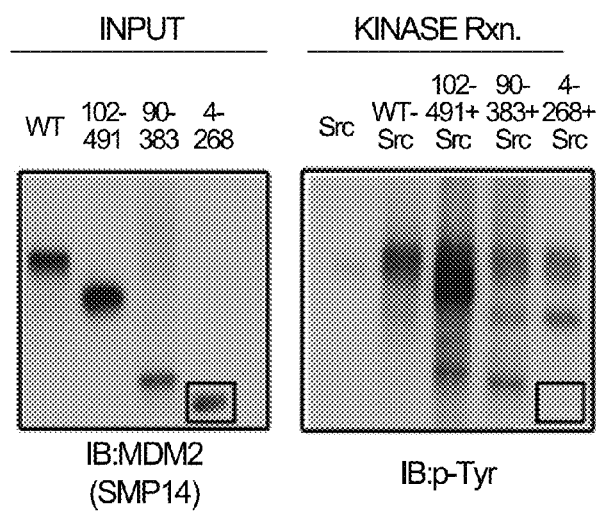
FIG. 5 is a Western blot of Mdm2 and phospho-tyrosines (p-Tyr) using in vitro phosphorylation reactions on truncated Mdm2 proteins as described in Example 4.
Figure 6:
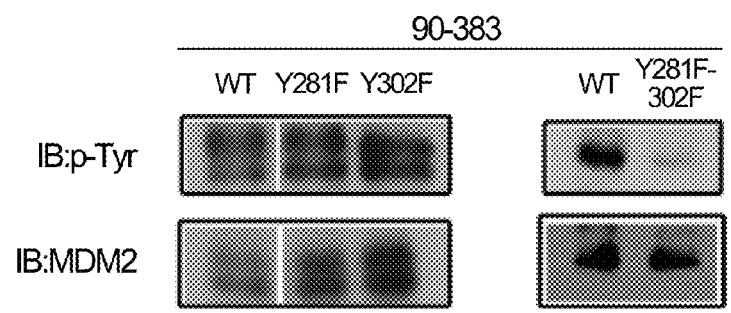
FIG. 6 is a Western blot of the in vitro kinase reaction with c-Src using the Y281F, Y302F or Y281F-302F 90-383 Mdm2 truncation mutants as described in Example 4.

The different mutants were incubated with c-Src and then immunoblot analysis was performed using an anti-phosphotyrosine antibody (4G10). The blot was then stripped and re-probed for Mdm2 (SMP14). Comparison of the blots revealed that the WT, 102-491, and 90-383 were all effectively phosphorylated by c-Src (FIG. 5). However, the Mdm2 truncation mutant 4-268 was unable to be phosphorylated by c-Src as indicated by the boxed regions (FIG. 5). Of note, the 4-268 mutant of Mdm2 still contains a SH3 binding domain and was able to bind to SH3-Src, thereby eliminating the possibility that the loss of tyrosine phosphorylation was a result of Src not binding to Mdm2. Thus, the in vitro kinase reaction narrowed down the potential c-Src phosphorylation site(s) to amino acids 268-393, which incorporates Y276, Y281, and Y302. Since c-Src and c-Abl have different recognition sequences and Y276 is already a known c-Abl phosphorylation site, this left Y281 and Y302 as potential c-Src phosphorylation sites. Site-directed mutagenesis was performed to determine which site is phosphorylated by c-Src. Y281F, Y302F, and an Y281-302F double mutant were created in the 90-383 truncated form of Mdm2 and used as substrates for an in vitro kinase reaction with c-Src. As shown in FIG. 6, the Y281-302F mutant was not phosphorylated by c-Src, while the single mutants were phosphorylated. Based on these results, the c-Src phosphorylation sites on Mdm2 are Y281 and Y302.

Example 5

In this Example, whether Mdm2 is an in vivo substrate for c-Src was determined.

First, H1299 cells were transfected with HA-tagged Mdm2 (HA-Mdm2) with either constitutively active c-Src (CA-Src) or a kinase dead Src (KD-Src). The CA-Src has a mutation at Y529F that prevents the normal down regulation of kinase activity and the KD-Src has a mutation at K297R, which results in catalytically inactive c-Src. An immunoprecipitation was then performed using the HA-tag followed by immunoblot analysis using anti-phosphotyrosine antibody (4G10). Along with overexpression, whether c-Src could phosphorylate endogenous Mdm2 was determined. For this second approach pharmacologic inhibition of c-Src was used. MCF7 cells were pretreated with the c-Src selective inhibitor PP1 for 16 hrs followed by immunoprecipitation with Mdm2. In addition, Maldi TOF mass spectrometry was used to determine if Y281 and Y302 of Mdm2 from MCF7 cells were phosphorylated.

Figure 7:
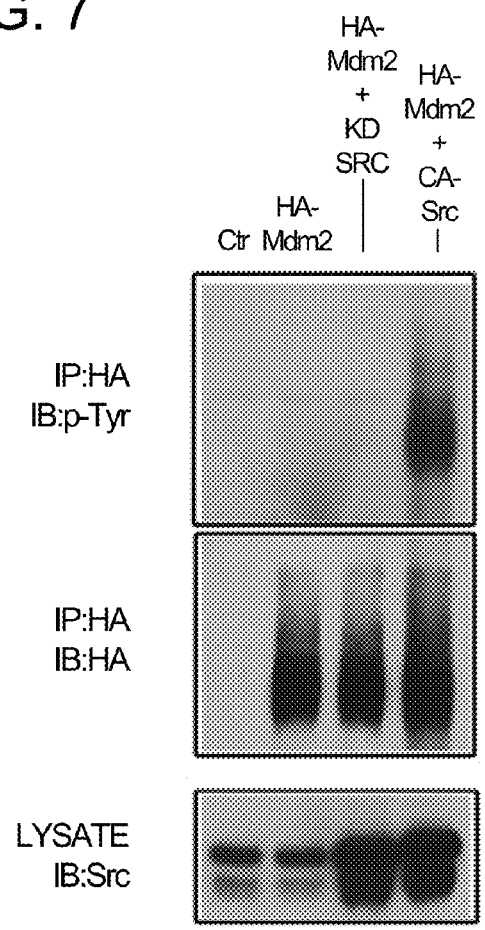
FIG. 7 is a Western blot of p-Tyr and HA from immunoprecipitation of HA-Mdm2 from transient transfections of H1299 cells with HA-Mdm2, KD-Src, or CA-Src as described in Example 5.
Figure 8:
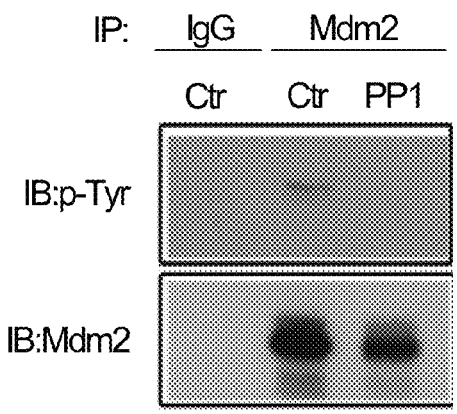
FIG. 8 is a Western blot of Mdm2 and p-Tyr after Mdm2 immunoprecipitation from MCF7 extracts after treatment with PP1 as described in Example 5.

Tyrosine phosphorylation of Mdm2 was observed in the presence of CA-Src, but not KD-Src (FIG. 7). Immunoblot analysis for phosphorylated tyrosine revealed that c-Src inhibition resulted in a loss of endogenous Mdm2 tyrosine phosphorylation (FIG. 8). Equivalent amounts of Mdm2 were observed after the immunoblot was re-probed for Mdm2 Phospho-peptides were recovered consistent with phosphorylated Y281 and Y302. Therefore, based on the in vitro and in vivo data, Mdm2 is a substrate for Src.

Example 6

In this Example, the effect of c-Src phosphorylation on Mdm2 protein levels was determined.

Figure 9:
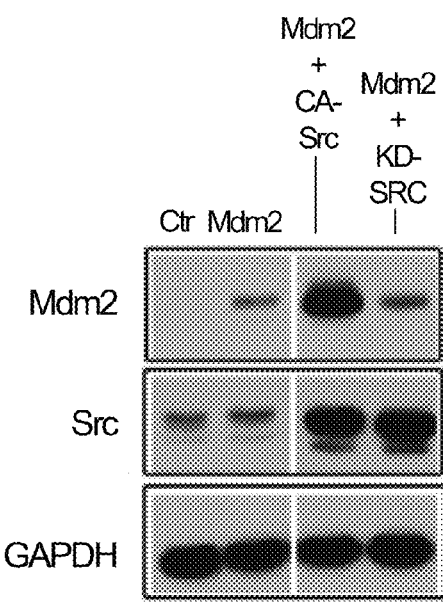
FIG. 9 is a Western blot of Mdm2, c-Src, and GAPDH from extracts of H1299 cells ectopically expressing Mdm2, CA-Src, or KD-Src as described in Example 6.

H1299 cells were transfected with Mdm2, Mdm2+CA-Src, or Mdm2+KD-Src. Western blot analysis showed an induction of Mdm2 protein levels in the presence of CA-Src, but not in the presence of KD-Src (FIG. 9).

Figure 10:
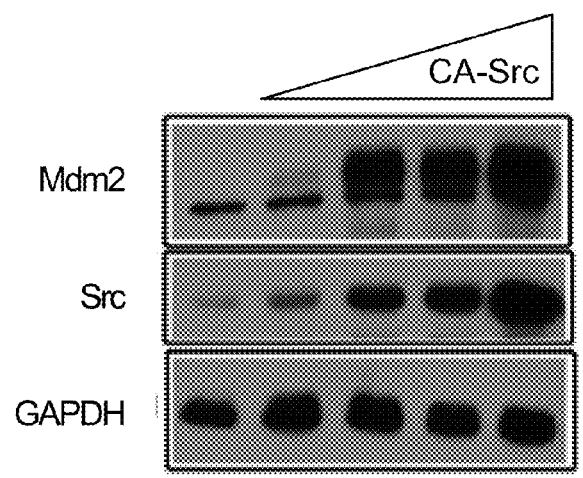
FIG. 10 is a Western blot of H1229 cells overexpressing Mdm2 and increasing concentrations (0.5, 1, 5, 10 µg) of CA-Src as described in Example 6.

To examine if an increase in c-Src activity would result in a dose-dependent increase in Mdm2 protein levels, H1299 cells were transfected with Mdm2 and then with increasing concentrations of CA-Src. Mdm2 protein levels increased concomitantly as c-Src levels increased (FIG. 10). It is noteworthy that the observed increases in Mdm2 protein levels are independent of p53 as H1299 cells are devoid of p53.

Figure 11:
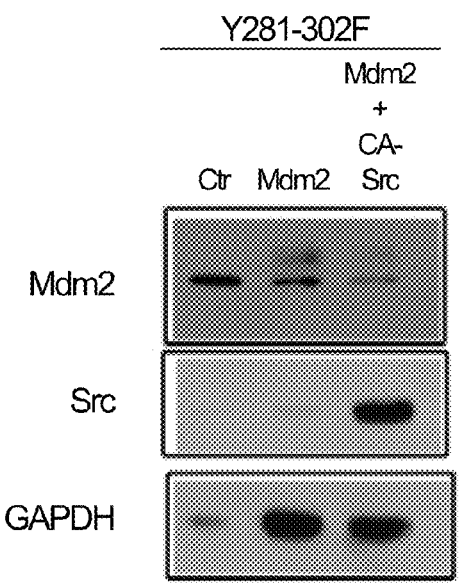
FIG. 11 is a Western blot of H1299 cells ectopically expressing Mdm2-Y281-302F and CA-Src as described in Example 6.

To verify that c-Src tyrosine phosphorylation of Mdm2 is required for the increase in Mdm2 protein levels, the Y281-302F Src-phosphorylation mutant of Mdm2 was used in transient transfection of H1299 cells. Overexpression of the Y281-302F, with or without CA-Src, in H1299 cells did not change Mdm2 protein levels (FIG. 11).

Figure 12:
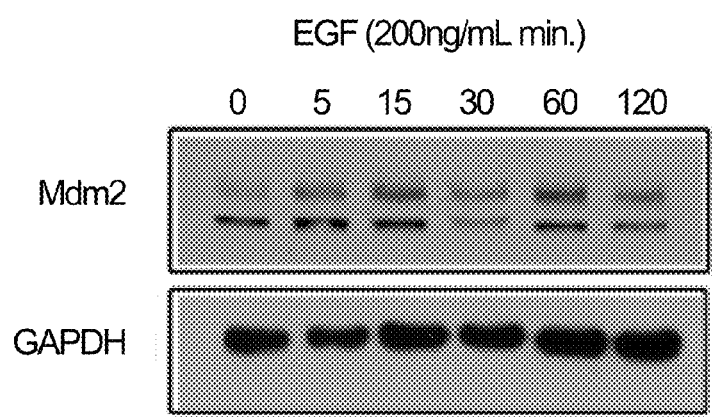
FIG. 12 is a Western blot of endogenous Mdm2 and GAPDH (for loading) from MCF7 cells treated with EGF for 0-120 minutes as described in Example 6.

To examine how c-Src regulates endogenous Mdm2 protein levels, c-Src was activated through epidermal growth factor (EGF) stimulation of MCF7 cells. MCF7 cells were serum-starved for 48 hrs and then treated with 200 ng/mL of EGF for a time course of 2 hrs. EGF stimulation resulted in an increase of Mdm2 protein levels with a peak achieved by 1 hr (FIG. 12).

Figure 13:
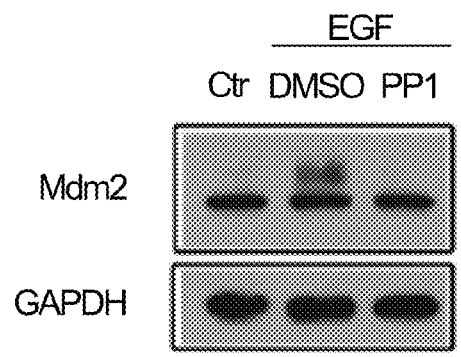
FIG. 13 is a Western blot for Mdm2 and GAPDH from MCF7 cells treated with either DMSO or PP1 prior to addition of EGF as described in Example 6.
Figure 14:
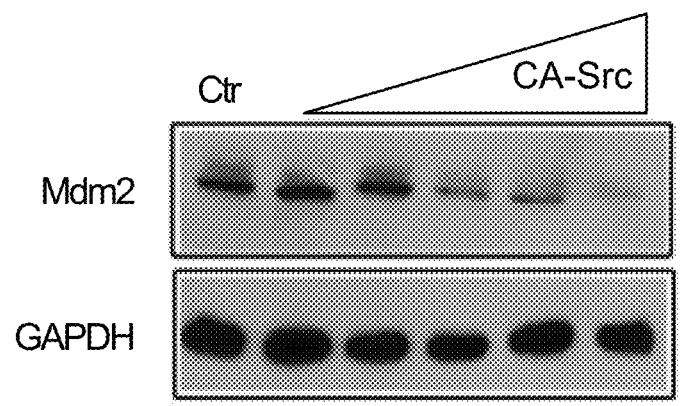
FIG. 14 is a Western blot for Mdm2 and GAPDH from MCF7 cells treated with increasing concentrations (1, 5, 10, 15, and 20 µM) of PP1 as described in Example 6.

To ensure that this increase of Mdm2 by EGF was due to c-Src activity, serum starved MCF7 cells were pre-treated with the c-Src inhibitor, PP1 or DMSO control for 1 hr before addition of EGF. While EGF alone resulted in an increase of Mdm2, use of PP1 showed no apparent increase in Mdm2 (FIG. 13). Since Mdm2 levels are increased due to c-Src activation, c-Src activity was inhibited to determine whether Mdm2 levels decreased. Treatment of MCF7 cells with increasing PP1 concentrations resulted in a dose-dependent decrease in Mdm2 levels (FIG. 14). Thus, the increase in Mdm2 protein level is due to activated c-Src and the phosphorylation of Mdm2.

Example 7

In this Example, the effect of c-Src on mdm2 gene expression and Mdm2 protein levels was determined.

Figure 15:
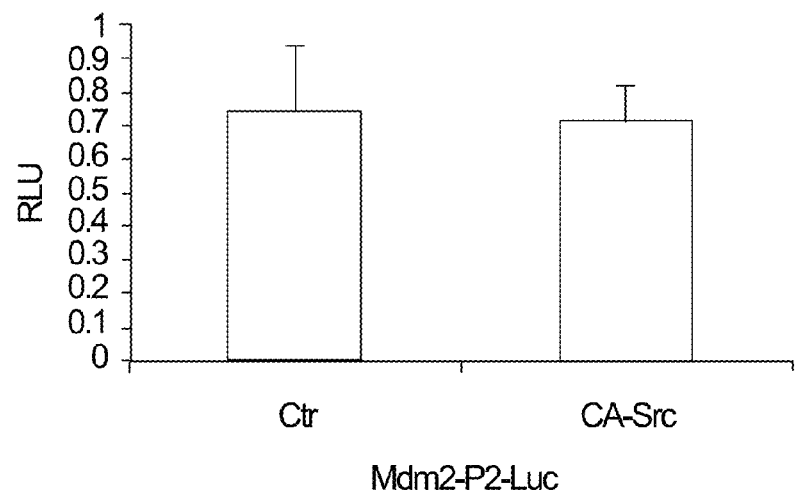
FIG. 15 is a graph depicting luciferase activity of mdm2-P2-Luc with Myc-LacZ in H1299 cells alone (Ctr) or expressing CA-Src as described in Example 7.
Figure 16:
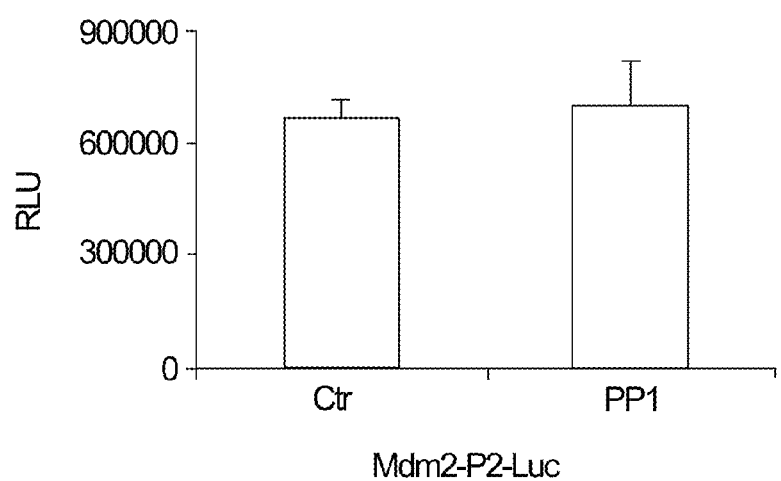
FIG. 16 is a graph depicting luciferase activity of mdm2-P2-Luc and Myc-LacZ in MCF7 cells after treatment with PP 1 or DMSO (Ctr) as described in Example 7.

To determine whether c-Src altered mdm2 gene expression, a luciferase reporter assay was conducted in which the mdm2 P2 promoter was attached to luciferase. No difference was observed in H1299 cells that were overexpressing c-Src (FIG. 15) or with inhibition of endogenous c-Src using PP1 treatment in MCF7 cells on the mdm2 promoter as determined by luciferase (FIG. 16). These results indicate that increasing Mdm2 levels are not due to increased gene expression.

To determine the effect of Src on the half-life of Mdm2, H1299 cells were transfected with Mdm2 plus Myc-LacZ for internal control and either CA-Src, KD-Src, or pUSE (Src vector control). After transfection (24 hours) the cells were treated with cyclohexamide for 2 hours to stop protein synthesis. The cells were then harvested at the indicated time points and subjected to immunoblotting to determine Mdm2 levels. The protein levels were quantified and graphed as a ratio of Mdm2/LacZ by measuring the intensity of each band.

Figure 17A:
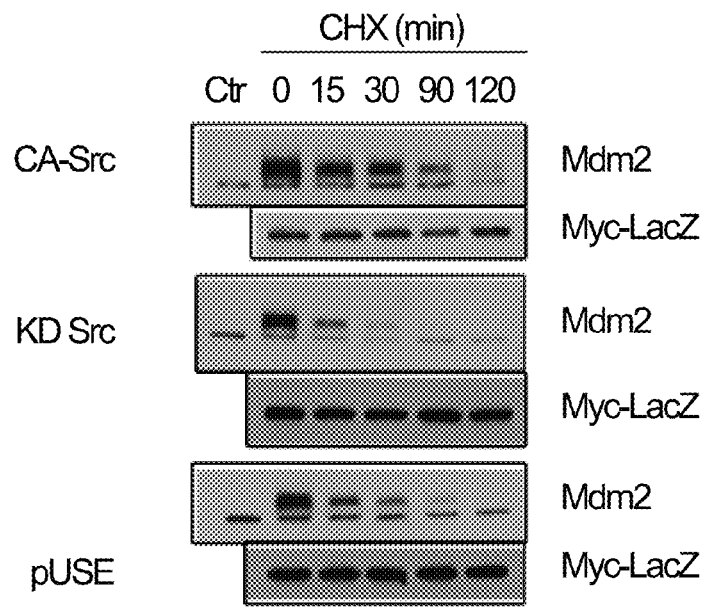
FIG. 17A is a Western blot probed with anti-Mdm2 and anti-Myc antibodies of H1299 cells transfected with Mdm2 and/or CA-Src, KD-Src or empty vector (pUSE) in the presence of Myc-LacZ vector treated with cyclohexamide (CHX) and harvested at 0-120 minutes as described in Example 7.
Figure 17B:
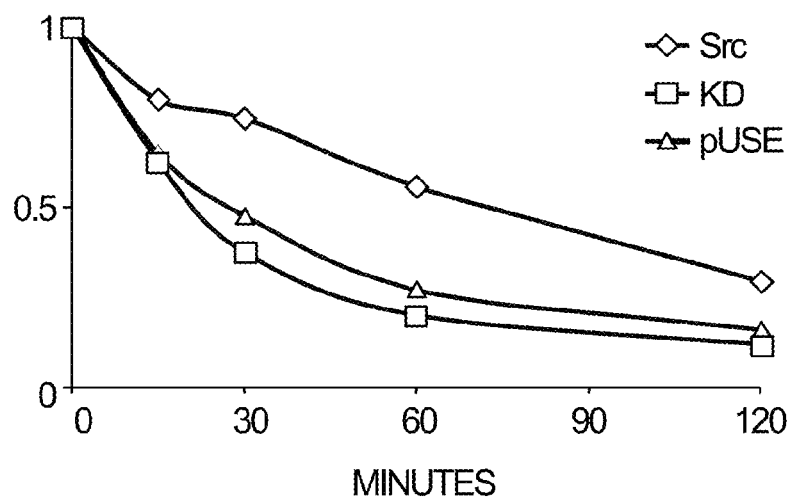
FIG. 17B is a graph depicting the density of Mdm2 in each lane from FIG. 17A versus the level of Myc-LacZ as described in Example 7.
Figure 18A:
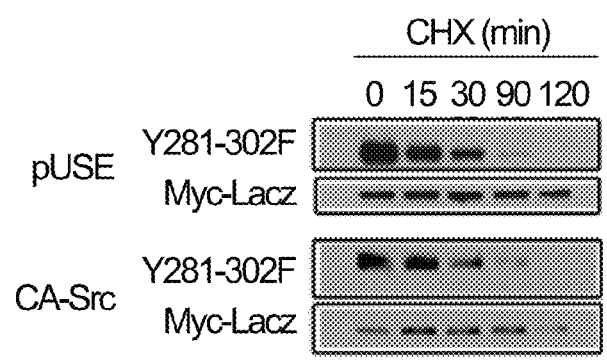
FIG. 18A is a Western blot probed with anti-Mdm2 and anti-Myc antibodies of H1299 cells transfected with Mdm2 mutant Y281-302F and/or CA-Src, KD-Src or empty vector (pUSE) in the presence of Myc-LacZ vector treated with cyclohexamide (CHX) and harvested at 0-120 minutes as described in Example 7.
Figure 18B:
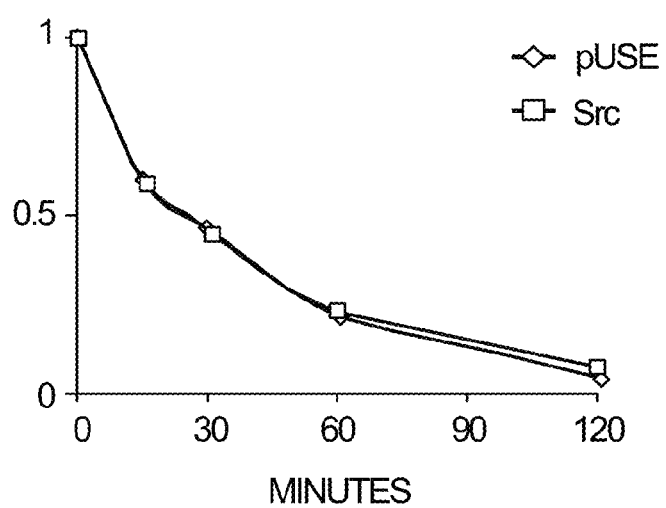
FIG. 18B is a graph depicting the density of Mdm2 in each lane from FIG. 17A versus the level of Myc-LacZ as described in Example 7.

In the presence of KD-Src the half-life of Mdm2 was 25 minutes, which is consistent with published reports of Mdm2 half-life. Interestingly, in the presence of CA-Src the half-life of Mdm2 increases to 70 minutes (FIGS. 17A & 17B). However, when the Mdm2 Y281-302F mutant was co-expressed with CA-Src, the half-life remained at 25 minutes, which was the same as wild-type Mdm2 (FIGS. 18A & 18B). Thus, Src-phosphorylation of Mdm2 more than doubled the half-life of Mdm2.

Figure 19A:
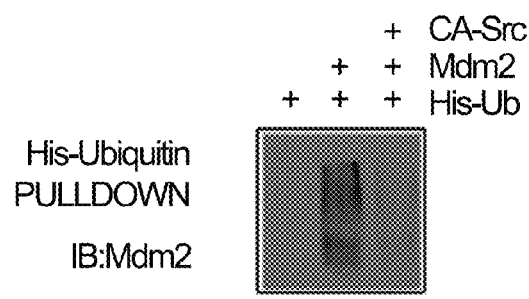
FIG. 19A is a Western blot of Mdm2 from a His-ubiquitin pull-down assay from H1299 cells transfected with Mdm2, CA-Src and His-ubiquitin.
Figure 19B:
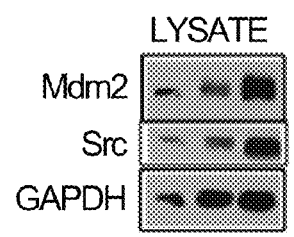
FIG. 19B is a Western blot of lysates probed for Mdm2, Src and GAPDH to verify expression as described in Example 7.

Since Mdm2 possesses the ability to function as an ubiquitin ligase, the effect of inhibiting Mdm2 loading with ubiquitin by c-Src phosphorylation on Mdm2 protein stability was determined. A transient assay was employed utilizing overexpressed and purified his-tagged ubiquitin protein conjugates. In the presence of CA-Src, Mdm2 ubiquitination was greatly reduced (FIGS. 19A & 19B). These experiments demonstrated that the increase in Mdm2 protein levels was due the lack of ubiquitin being loaded to Mdm2.

Example 8

In this Example, whether phosphorylation of Mdm2 by c-Src could serve as an E3 ubiquitin ligase towards p53 was determined.

Figure 20:
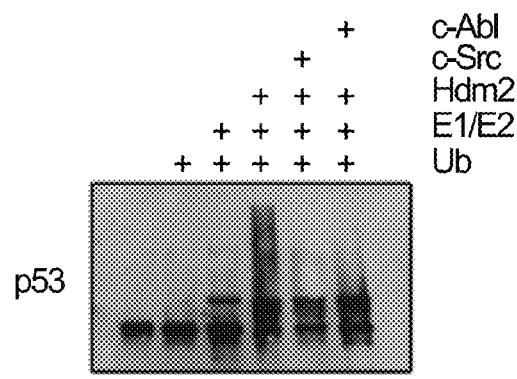
FIG. 20 is a Western blot of p53 (D01) from an in vitro ubiquitination assay performed with recombinant p53 using Mdm2 or Mdm2 phosphorylated by c-Src/c-Abl as described in Example 8.

An in vitro ubiquitination assay of p53 was performed using untreated or phosphorylated Mdm2 Phosphorylation was performed with c-Src or c-Abl. c-Abl is known to inhibit Mdm2 ubiquitination of p53, and thus served as a positive control. Phosphorylation with c-Src inhibited the ubiquitination of p53 to the same extent as c-Abl (FIG. 20).

Figure 21:
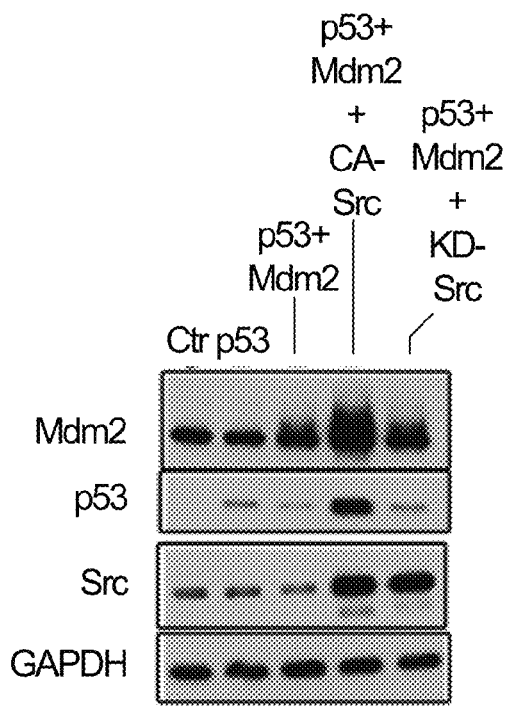
FIG. 21 is a Western blot analysis of lysates from H1299 cells overexpressing p53, Mdm2, CA-Src, and KD-Src as described in Example 8.

Since Mdm2 was unable to ubiquitinate p53 in vitro, the effect on p53 protein levels in cells was determined H1299 cells were transfected with different combinations of p53, Mdm2, CA-Src, and KD-Src. Addition of Mdm2 resulted in a decrease of p53, but CA-Src prevented p53 from Mdm2-mediated degradation, while KD-Src had no such effect (FIG. 21).

Figure 22:
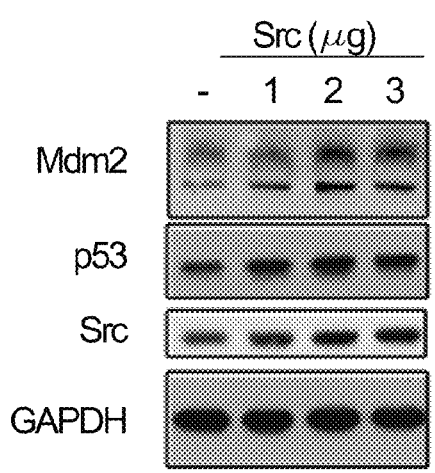
FIG. 22 is a Western blot showing endogenous levels of Mdm2, p53, GAPDH, and expression of Src from lysates of MCF7 cells ectopically expressing CA-Src as described in Example 8.
Figure 23:
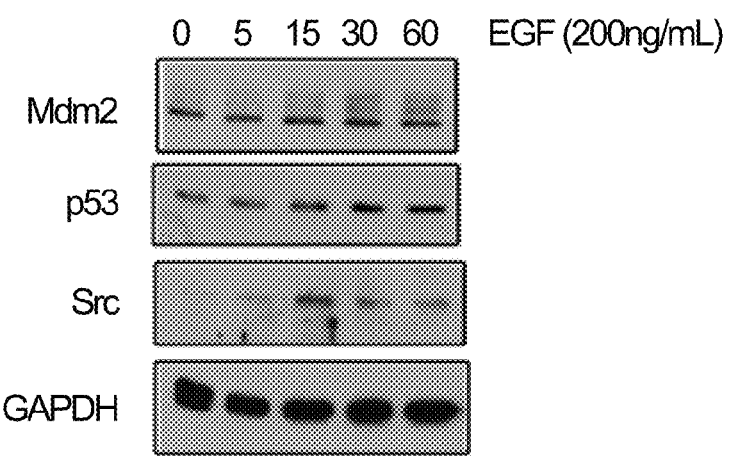
FIG. 23 is a Western blot of Mdm2, p53, activated Src (p-Src Y408) and GAPDH from MCF7 cells serum starved for 48 hours and incubated with EGF over a time course of 0-60 minutes as described in Example 8.
Figure 24:
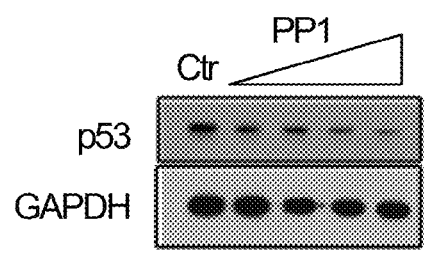
FIG. 24 is a Western blot of p53 from MCF7 cell extracts treated with increasing concentrations of PP1 (1, 5, 10, 15, 20 µM) as described in Example 8.

To examine endogenous p53 levels, MCF 7 cells were transfected with increasing amounts of CA-Src. As observed with the overexpression, endogenous levels of p53 increased with c-Src expression and this increase of p53 correlated directly with the increase of Mdm2 (FIG. 22). Furthermore, activation of endogenous c-Src by EGF over a 1-hour time course resulted in a similar increase in p53 that mimics the activation of c-Src and Mdm2 protein levels (FIG. 23). Additionally, inhibition of endogenous c-Src with PP1 resulted in a dose dependent decrease in p53 levels (FIG. 24). These results support the observation that c-Src phosphorylation of Mdm2 results in stabilization of p53 levels due to Mdm2 inability to function as an ubiquitin ligase.

Figure 25:
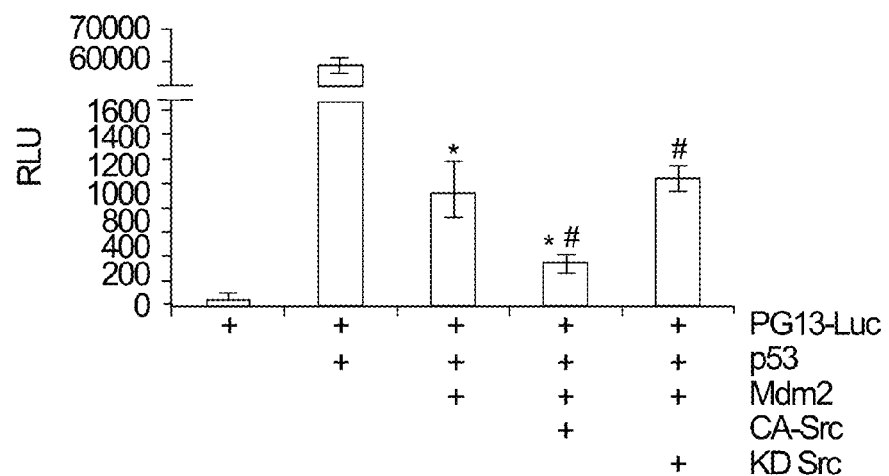
FIG. 25 is a graph depicting luciferase activity using PG13-synthetic (PG13-Luc) promoter and Myc-LacZ in H1299 cells transfected with p53, Mdm2, CA-Src, and KD-Src as described in Example 8 (*,# represents statistical significance of p<0.05; Y-axis measurements are relative luciferase units (RLU) calculated from the ratio of luciferase/β-gal activity; error bars represent standard deviation).

Since Mdm2 could not ubiquitinate p53, whether this stability coincided with an increase in p53 activity was determined. Using PG13-Luc, which is an artificial p53 promoter attached to luciferase, along with combinations of p53, Mdm2, CA-Src and KD-Src, p53 activity was decreased in the presence of Mdm2 However, p53 activity was further decreased by an additional 60% in the presence of CA-Src and reverted to the same level of Mdm2 alone in the presence of KD-Src. These data show that Mdm2 inhibition of p53 is further enhanced in the presence of CA-Src (FIG. 25), even though p53 protein levels are stabilized.

Figure 26:
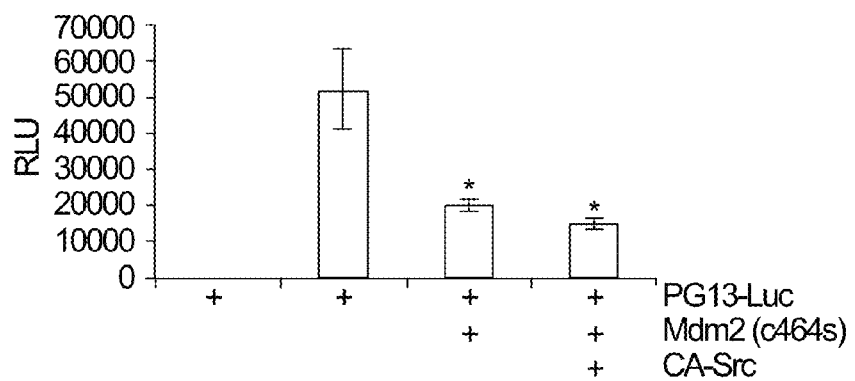
FIG. 26 is a graph depicting luciferase activity using PG13-Luc and Myc-LacZ in H1299 cells transfected with p53, Mdm2 (C464S), and CA-Src as described in Example 8 (*,# represents statistical significance of p<0.05; Y-axis measurements are relative luciferase units (RLU) calculated from the ratio of luciferase/β-gal activity; error bars represent standard deviation).

Although Mdm2 can inhibit p53 through binding, the Src-phosphorylation sites suggest that inhibition of binding is not dependent on increasing the p53-Mdm2 complex. To test if this was evident, a luciferase assay using the ligase dead mutant C464S of Mdm2 was conducted. H1299 cells were transfected with the PG-13-Luc along with p53, C464S, and CA-Src. The luciferase assay showed that p53 activity was decreased in the presence of C464S Mdm2 but was not dramatically increased with CA-Src (FIG. 26). This experiment provides direct evidence that there is a dependence on the Mdm2's RING for c-Src to fully inactivate p53.

Example 9

In this Example, whether Mdm2 phosphorylated by c-Src could function as a neddylating enzyme was determined.

Figure 27A:
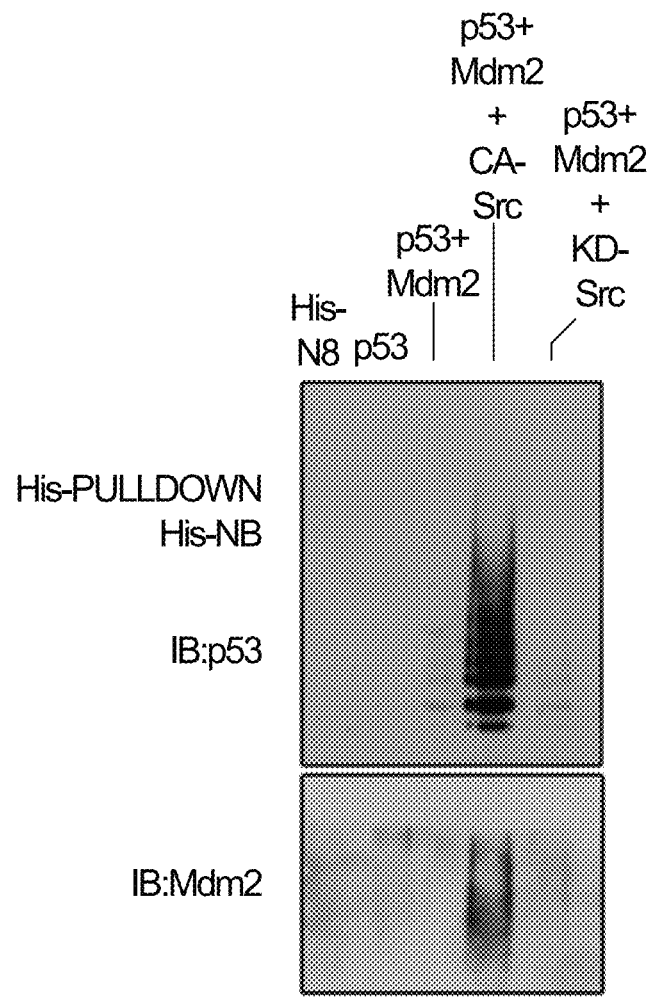
FIG. 27A is a Western blot of p53 and Mdm2 from His-Nedd8 pulldown assay of H1299 cells expressing His-Nedd8, p53, WT-Mdm2, Mdm2 Y281-302F, CA-Src, and KD-Src as described in Example 9.
Figure 27B:
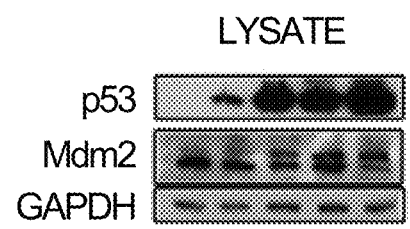
FIG. 27B is a Western blot of p53, Mdm2 and GAPDH to verify expression as described in Example 9.

H1299 cells were transfected with a His-Nedd8 construct along with p53, Mdm2, and CA-Src or KD-Src. A nickel pulldown assay was used to isolate neddylated proteins. Blots were probed for p53 or Mdm2 (FIG. 27A) and blots of lysates were probed for p53, mdm2 and GAPDH to verify expression (FIG. 27B). In the presence of CA-Src, neddylated p53 dramatically increased (FIG. 27A). When the immunoblot was stripped and re-probed with anti-Mdm2 antibodies, an increase in Mdm2-Nedd8 conjugates in the presence of CA-Src was detected (FIG. 27A). Interestingly, Nedd8 conjugated to p53 or Mdm2 was absent when KD-Src was present (FIG. 27). These results indicate that c-Src phosphorylation of Mdm2 activates the neddylating activity of Mdm2.

Figure 28:
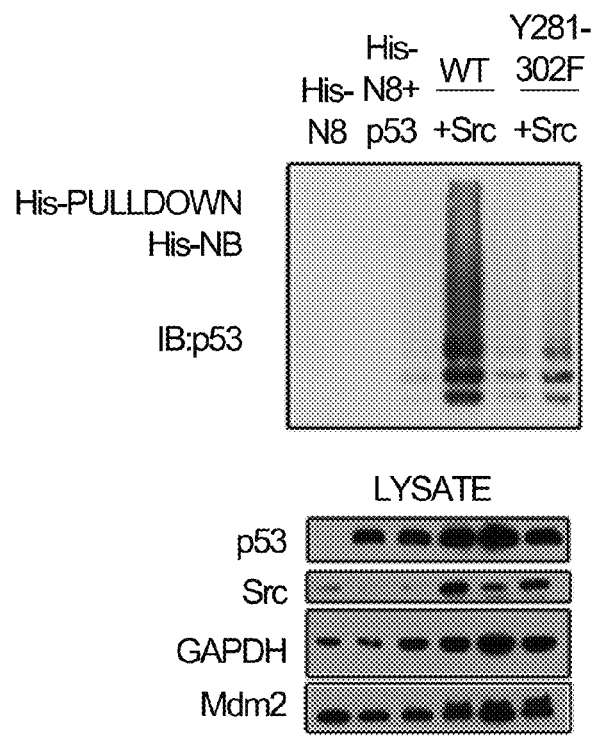
FIG. 28 is a Western blot of p53 and Mdm2 from His-Nedd8 pulldown assay using Mdm2-Y281-302F as described in Example 9.

To provide further evidence that the switch of Mdm2 activity was dependent on Src-phosphorylation of Mdm2, a His-Nedd8 pulldown assay using the phosphorylation deficient mutant Y281-302F was performed. Results showed that p53 neddylation increased dramatically in the presence of wild-type Mdm2 and CA-Src, but there was no change in p53 neddylation in the presence of Y281-302F and CA-Src (FIG. 28).

Figure 29:
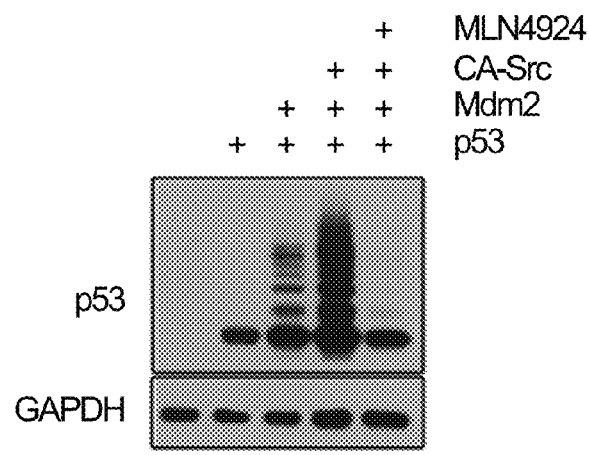
FIG. 29 is a Western blot of p53 from H1299 overexpressing p53, Mdm2, and CA-Src treated with either DMSO or MLN4924 as described in Example 9.

Based on transient transfection data that supported its role as a neddylating enzyme, the affect of pharmacological inhibition of neddylating activity of Mdm2 using MLN4924 was determined. Treatment of H1299 cells transfected with p53, Mdm2, and CA-Src with MLN4924 resulted in the loss of neddylated p53 (FIG. 29).

Figure 30:
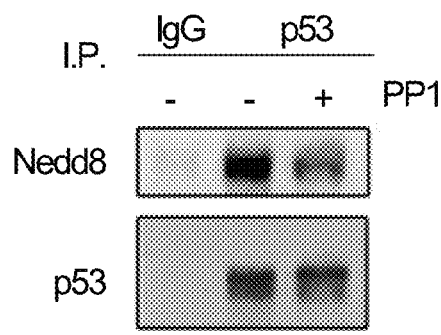
FIG. 30 is a Western blot of Nedd8 and p53 from immunoprecipitation of p53 from MCF7 cells treated with PP1 or DMSO as described in Example 9.

To determine the role of c-Src on endogenous neddylation of p53, the c-Src inhibitor PP1 was used to treat MCF7 cells. MCF7 cells were treated with PP1, and p53 was immunoprecipitated from cell extracts. Immunoblot analysis was done using anti-Nedd8. Inhibition of c-Src using PP1 resulted in a decrease in endogenous neddylated p53 (FIG. 30).

Figure 31:
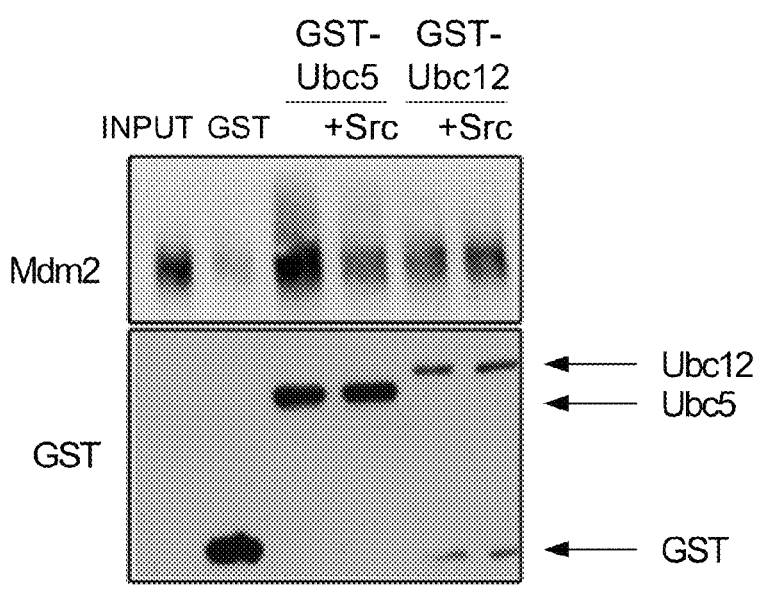
FIG. 31 is a Western blot of a GST-pulldown of GST-UbcS and GST-Ubc12 with Mdm2 or c-Src phosphorylated Mdm2 as described in Example 9.

Since Mdm2 ligase activity is specified by which E2 (ubiquitin or neddylation) it binds, whether c-Src phosphorylation of Mdm2 might inhibit or enhance interactions with a specific E2 was determined. Recombinant GST-UbcS (ubiquitin E2) and GST-Ubc12 (neddylation E2) were incubated with Mdm2 or phosphorylated Mdm2 and a GST pulldown assay was performed. c-Src phosphorylation of Mdm2 resulted in a substantial decrease in the UbcS/Mdm2 interaction compared to unphosphorylated Mdm2 (FIG. 31). The Ubc12/Mdm2 interaction showed a slight increase after Mdm2 phosphorylation. These results provide evidence that the mechanism of c-Src activation of Mdm2 ligase activity may be due to changes in specific E2 recruitment. Taken together, these results show that c-Src phosphorylation of Mdm2 actives the neddylation activity of Mdm2.

Example 10

In this Example, the effect of inhibition of neddylation on p53 activity was determined.

Figure 32:
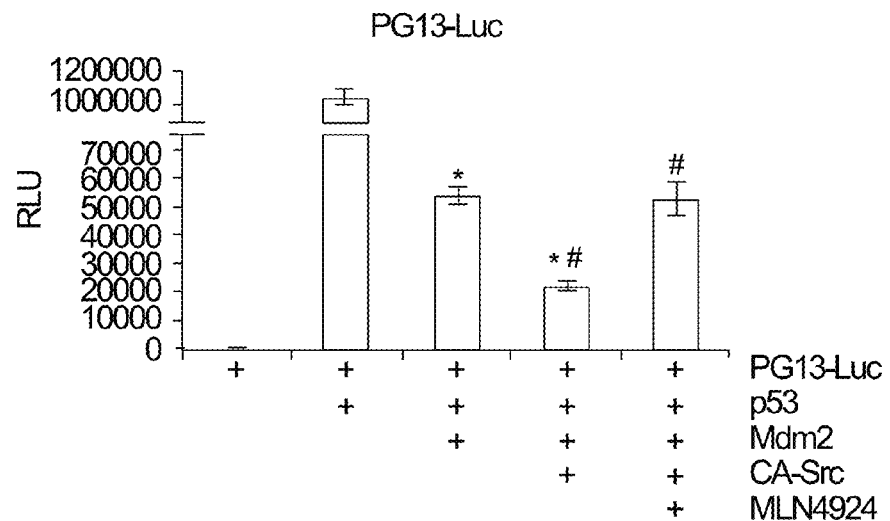
FIG. 32 is a graph depicting PG13-Luc activity assayed using H1299 cells transfected with Myc-LacZ, p53, Mdm2, and CA-Src treated with DMSO or MLN4924 as described in Example 10 (*, # represents statistical significance of p<0.05; Y-axis measurements are relative luciferase units (RLU) calculated from the ratio of luciferase/β-gal activity; error bars represent standard deviation).

H1299 cells were transfected with the PG-13-luc, p53, Mdm2 and CA-Src. Reduction in p53 activity by Mdm2 was further increased in the presence of c-Src. Treatment with MLN4924 restored p53 activity to levels observed with Mdm2 alone, which demonstrates a Src-Mdm2-Nedd8 pathway that inactivates p53 (FIG. 32).

Example 11

In this Example, the effect of Mdm2 phosphorylated by Src on the induction of p53 on a more relevant physiological target was determined.

The tumor suppressor maspin is a p53 target that plays an important role in regulating tumor cell invasion and metastasis. To assess Src-phosphorylated Mdm2 effect on p53-induced maspin, a luciferase assay utilizing the maspin promoter was performed.

Figure 33:
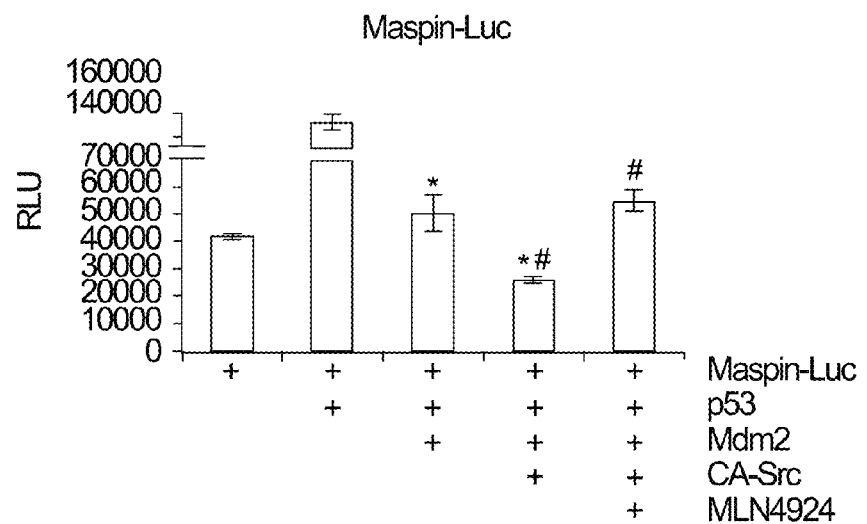
FIG. 33 is a graph depicting Maspin-Luc activity assayed using H1299 cells transfected with Myc-LacZ, p53, Mdm2, and CA-Src treated with DMSO or MLN4924 as described in Example 11 (*, # represents statistical significance of p<0.05; Y-axis measurements are relative luciferase units (RLU) calculated from the ratio of luciferase/β-gal activity; error bars represent standard deviation).

As shown in FIG. 7B, H1299 cells transfected with the maspin promoter attached to the luciferase gene (maspin-Luc) showing that p53 drives the expression of luciferase from the maspin promoter and that a decrease is seen with Mdm2 overexpression (FIG. 33). As with the PG13-Luc synthetic construct, expression of CA-Src further inhibits p53 activity on the maspin promoter and the inhibition is dependent on neddylation.

Figure 34:
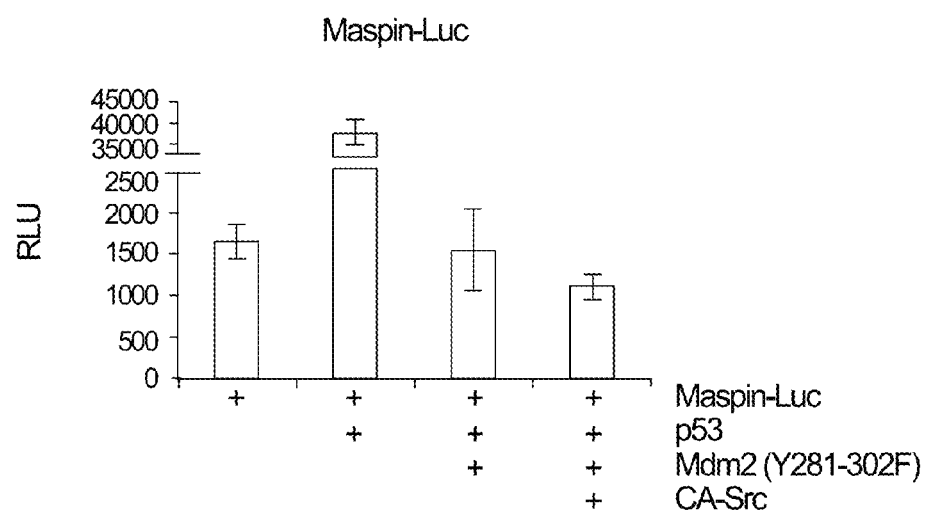
FIG. 34 is a graph depicting luciferase activity of Maspin-Luc in H1299 cells using p53, Mdm2 Y281-302F, and CA-Src as described in Example 11 (*, # represents statistical significance of p<0.05; Y-axis measurements are relative luciferase units (RLU) calculated from the ratio of luciferase/β-gal activity; error bars represent standard deviation).
Figure 35:
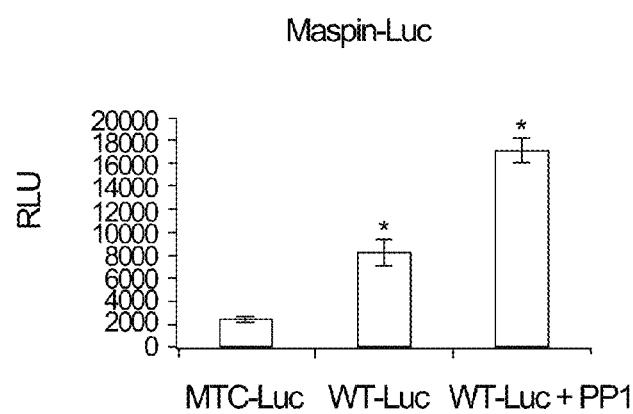
FIG. 35 is a graph depicting luciferase activity of MCF7 transfected with either Maspin-Luc or Mutant Maspin-Luc (MTC) and Myc-LacZ treated with DMSO or PP1 as described in Example 11 (*, # represents statistical significance of p<0.05; Y-axis measurements are relative luciferase units (RLU) calculated from the ratio of luciferase/β-gal activity; error bars represent standard deviation).
Figure 36:
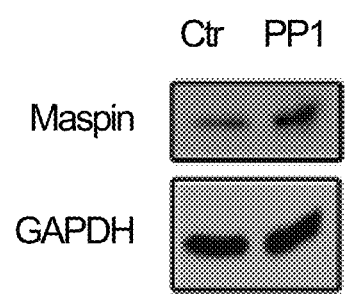
FIG. 36 is a Western blot for Maspin and GAPDH from MCF7 cells treated with DMSO or PP1 as described in Example 11.
Figure 37:
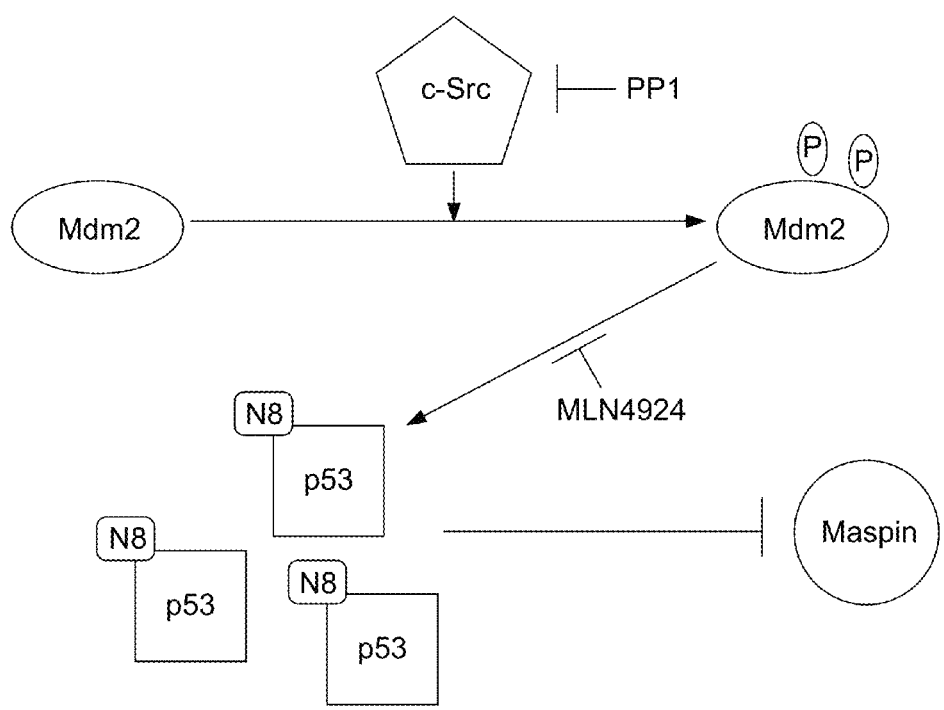
FIG. 37 is a schematic illustrating a model depicting c-Src phosphorylation of Mdm2 and its downstream signaling pathway as described in Example 11.

To ensure that the decrease seen on the maspin promoter was due to c-Src phosphorylation of Mdm2, another luciferase assay was done using the Y281-302F Mdm2 and CA-Src. Here the maspin promoter luciferase decreased with the addition of Mdm2 Y281-Y302F, but the addition of c-Src did not result in an increase of inhibition as seen with wild-type Mdm2 (FIG. 34). These results demonstrate that the enhancement of inhibition observed on the maspin promoter by c-Src is dependent on Mdm2 Y281 and Y302. For further insight on how endogenous neddylation of p53 would affect maspin level, MCF7 cells were transfected with the maspin-Luc construct or a mutant maspin-Luc (MT1) that is unresponsive to p53, to ensure luciferase activity was dependent on p53. c-Src was then inhibited for 16 hrs using PP1 and a luciferase assay was performed. Inactivation of c-Src allowed for an increase of p53 activity on the maspin-Luc construct (FIG. 35). This increase of p53 activity was also observed at the protein level, as maspin protein was increased following inhibition of c-Src (FIG. 36). These findings provide insight into the regulation of c-Src-induced neddylation of p53. This neddylation event is responsible for the further reduction in p53 activity on both the PG13-Luc and on its ability to activate the tumor suppressor maspin (FIG. 37).

Example 12

In this Example, Mdm2 neddylating enzyme function and conjugation of nedd8 to HIF1α was determined.

Figure 38A:
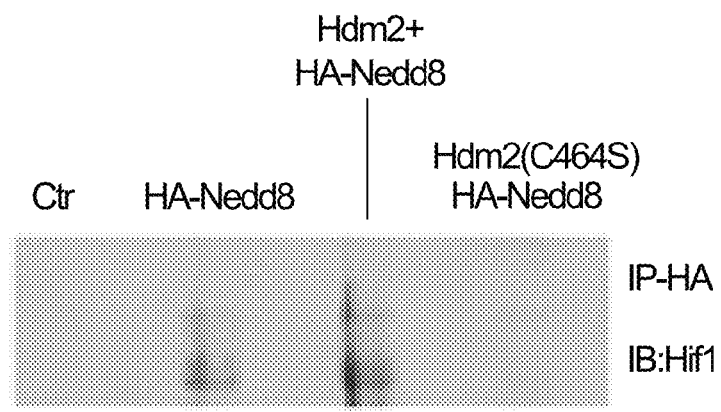
FIG. 38A is a Western blot of HIF1α from immunoprecipitation of HA-nedd8 as described in Example 12.
Figure 38B:
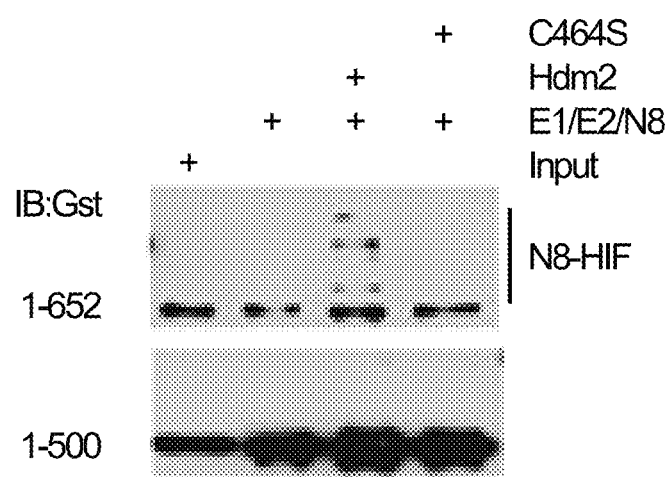
FIG. 38B is a Western blot showing in vitro neddylation reaction with 1-652 and 1-500 GST-HIF1α in the presence of Mdm2 (Hdm2) and catalytically dead Mdm2 (C464S) as described in Example 12.
Figure 39:
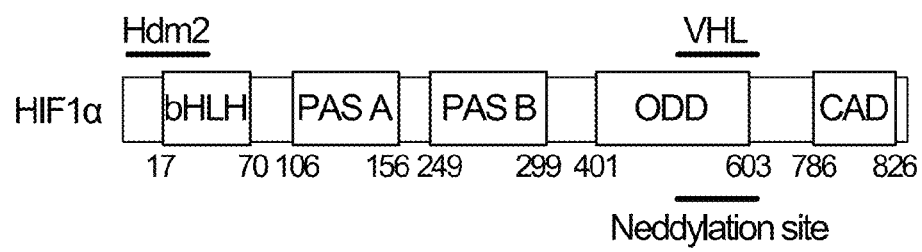
FIG. 39 is a schematic illustrating the domain structure of HIF1α and the binding sites for Mdm2, pVHL and the putative neddylation domain.

Using HA-tagged nedd8 transfected into cells subjected to hypoxia (1% oxygen), HA was immunoprecipitated and HIF1α was detected by western blot (FIGS. 38A & 38B). Mdm2 conjugated nedd8 to HIF1α which was dependent on the E3 ligase activity of Mdm2 as the enzymatically dead C464S mutant of Mdm2 did not neddylate HIF1α and this modification in HIF1α occurred in the oxygen-dependent domain (ODD) (FIGS. 38A-B). This domain is important for binding to pVHL (see, FIG. 39).

Figure 40A:
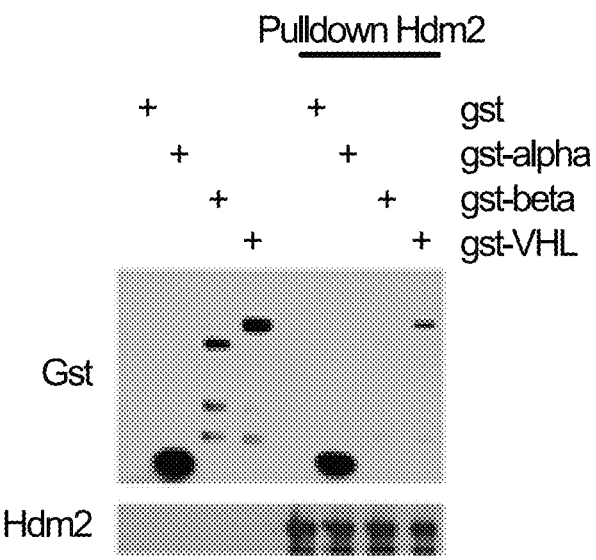
FIG. 40A is a Western blot of GST-tagged VHL and truncated versions (alpha and beta domain) as described in Example 12.
Figure 40B:
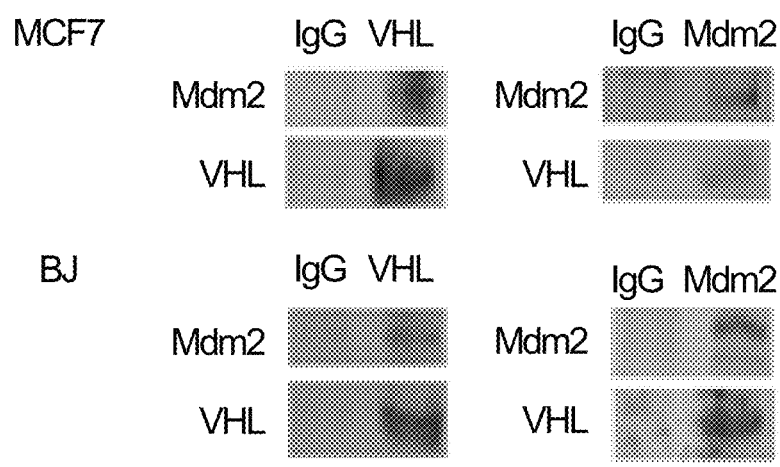
FIG. 40B is a Western blot of Mdm2 and pVHL immunoprecipted from MCF7 or BJ cells.
Figure 41:
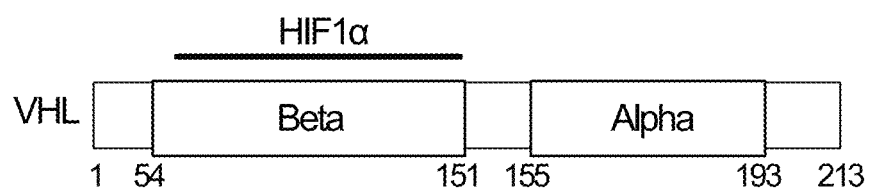
FIG. 41 is a schematic illustrating the domain structure of VHL and the binding site for HIF1α.

Since, pVHL is an important tumor suppressor, pVHL binding to Mdm2 was determined. Using recombinant truncated purified GST-pVHL proteins, Mdm2 formed a complex with pVHL via the alpha domain of pVHL (FIG. 40A and FIG. 41). To examine whether the Mdm2-pVHL interaction was evident in cells, Mdm2 or pVHL was immunoprecipitated from MCF7 or human fibroblast (BJ) cells and counter blotted for pVHL or Mdm2. The results demonstrated that Mdm2 and pVHL formed a complex endogenously (FIG. 40B). These data indicated that Mdm2 regulates the activity of HIF1α enzymatically, and also physically prevents the association of pVHL with HIF1α.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of identifying a compound that modulates murine double-minute 2 neddylation activity, the method comprising providing a cell transfected with a nucleic acid encoding murine double-minute 2; contacting the cell with a test compound; and determining murine double-minute 2 phosphorylation at a tyrosine selected from the group consisting of Y281, Y302 and combinations thereof.

2. The method of claim 1, wherein murine double-minute 2 phosphorylation is increased as compared to murine double-minute 2 phosphorylation in the absence of the protein kinase and the test compound.

3. The method of claim 1, wherein murine double-minute 2 phosphorylation is decreased as compared to murine double-minute 2 phosphorylation in the absence of the protein kinase and the test compound.

4. The method of claim 1, further comprising determining murine double-minute 2 neddylation activity.

5. The method of claim 4, wherein the murine double-minute 2 neddylation activity selectively increases neddylation of a tumor suppressor.

6. The method of claim 5, wherein the tumor suppressor is selected from the group consisting of p53, maspin, p73, Von Hippel-Lindau and combinations thereof.

7. The method of claim 4, wherein murine double-minute 2 neddylation activity selectively decreases neddylation of a tumor suppressor.

8. The method of claim 7, wherein the tumor suppressor is selected from the group consisting of p53, maspin, p73, Von Hippel-Lindau and combinations thereof.

9. The method of claim 1, wherein the cell is an MCF7 cell.

10. The method of claim 1, wherein the cell is further transfected with a nucleic acid encoding a protein selected from the group consisting of Cellular Rouse sarcoma viral oncogene homolog (c-Src), p53, Ableson tyrosine kinase, Ableson-related protein and Hematopoietic cell kinase.

11. A method of identifying a compound that modulates murine double-minute 2 neddylation activity, the method comprising: contacting murine double-minute 2 with a protein kinase and a test compound; and determining murine double-minute 2 phosphorylation at a tyrosine selected from the group consisting of Y281, Y302 and combinations thereof.

12. The method of claim 11, wherein murine double-minute 2 phosphorylation is increased as compared to murine double-minute 2 phosphorylation in the absence of the protein kinase and the test compound.

13. The method of claim 11, wherein murine double-minute 2 phosphorylation is decreased as compared to murine double-minute 2 phosphorylation in the absence of the protein kinase and the test compound.

14. The method of claim 11, wherein the protein kinase is selected from the group consisting of Cellular Rouse sarcoma viral oncogene homolog (c-Src), Ableson tyrosine kinase, Ableson-related protein and Hematopoietic cell kinase.

15. The method of claim 11, further comprising determining murine double-minute 2 ubiquitination of a tumor suppressor.

16. The method of claim 15, wherein the tumor suppressor is selected from the group consisting of p53, maspin, p73, Von Hippel-Lindau and combinations thereof.

17. The method of claim 15, wherein murine double-minute 2 ubiquitination of the tumor suppressor is increased in the presence of the test compound as compared to murine double-minute 2 ubiquitination in the absence of the test compound.

18. The method of claim 15, wherein murine double-minute 2 ubiquitination of the tumor suppressor is decreased in the presence of the test compound as compared to murine double-minute 2 ubiquitination in the absence of the test compound.

19. The method of claim 11, further comprising determining murine double-minute 2 neddylation of a tumor suppressor.

20. The method of claim 19, wherein the tumor suppressor is selected from the group consisting of p53, maspin, p73, Von Hippel-Lindau and combinations thereof.

* * * * *